(12) United States Patent
Passini et al.

(10) Patent No.: US 10,821,154 B2
(45) Date of Patent: Nov. 3, 2020

(54) COMPOSITIONS AND METHODS FOR TREATING SPINAL MUSCULAR ATROPHY

(71) Applicant: Genzyme Corporation, Cambridge, MA (US)

(72) Inventors: Marco A. Passini, Northborough, MA (US); Lamya S. Shihabuddin, West Newton, MA (US); Catherine R. O'Riordan, Waban, MA (US); Seng H. Cheng, Natick, MA (US)

(73) Assignee: Genzyme Corporation, Cambridge, MA (US)

( * ) Notice: Subject to any disclaimer, the term of this patent is extended or adjusted under 35 U.S.C. 154(b) by 65 days.

(21) Appl. No.: 14/888,385

(22) PCT Filed: May 1, 2013

(86) PCT No.: PCT/US2013/039163
§ 371 (c)(1),
(2) Date: Feb. 8, 2016

(87) PCT Pub. No.: WO2014/178863
PCT Pub. Date: Nov. 6, 2014

(65) Prior Publication Data
US 2016/0074474 A1    Mar. 17, 2016

(51) Int. Cl.
*A61K 38/17* (2006.01)
*A61K 48/00* (2006.01)
*A61K 9/00* (2006.01)

(52) U.S. Cl.
CPC ........ *A61K 38/1709* (2013.01); *A61K 9/0019* (2013.01); *A61K 9/0085* (2013.01); *A61K 48/0058* (2013.01); *A61K 48/0075* (2013.01); *A61K 48/00* (2013.01); *C12N 2750/14141* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS

| | | |
|---|---|---|
| 5,328,470 A | 7/1994 | Nabel et al. |
| 6,566,118 B1 | 5/2003 | Atkinson et al. |
| 6,596,535 B1 | 7/2003 | Carter |
| 6,989,264 B2 | 1/2006 | Atkinson et al. |
| 6,995,006 B2 | 2/2006 | Atkinson et al. |
| 7,125,717 B2 | 10/2006 | Carter |
| 7,765,583 B2 | 7/2010 | Kalonji et al. |
| 7,785,888 B2 | 8/2010 | Carter |
| 7,790,154 B2 | 9/2010 | Samulski et al. |
| 7,846,729 B2 | 12/2010 | Carter |
| 8,093,054 B2 | 1/2012 | Carter |
| 8,361,457 B2 | 1/2013 | Samulski et al. |
| 9,415,119 B2 | 8/2016 | Passini et al. |
| 10,369,193 B2 | 8/2019 | Passini |
| 2013/0287736 A1 | 10/2013 | Passini et al. |
| 2017/0087212 A1 | 3/2017 | Passini et al. |

FOREIGN PATENT DOCUMENTS

| | | |
|---|---|---|
| WO | WO-03/004660 A1 | 1/2003 |
| WO | WO-2006/119341 A2 | 11/2006 |
| WO | WO-2007/146046 A2 | 12/2007 |
| WO | WO-2009/013290 A1 | 1/2009 |
| WO | WO-2010/071832 A1 | 6/2010 |
| WO | WO-2010/129021 A1 | 11/2010 |

OTHER PUBLICATIONS

Amado, D. et al. (Mar. 3, 2010). "Safety and Efficacy of Subretinal Readministration of a Viral Vector in Large Animals to Treat Congenital Blindness," *Sci. Transl. Med.* 2(21):21ra16.
Avila, A.M. et al. (Mar. 2007). "Trichostatin A Increases SMN Expression and Survival in a Mouse Model of Spinal Muscular Atrophy," *J. Clin. Invest.* 117(3):659-671.
Bankiewicz, K.S. et al. (Oct. 2006, e-pub. Jul. 7, 2006). "Long-term clinical improvement in MPTP-lesioned primates after gene therapy with AAVhAADC," *Mol. Ther.* 14, 564-570.
Bebee, T.W. et al. (2012, e-pub. Apr. 29, 2012). "Mouse models of SMA: tools for disease characterization and therapeutic development," Hum. Genet. 131:1277-1293.
Benkhelifa-Ziyyat, S. et al. (Feb. 2013, e-pub. Jan. 8, 2013). "Intramuscular scAAV9-SMN Injection Mediates Widespread Gene Delivery to the Spinal Cord and Decreases Disease Severity in SMA Mice," *Molecular Therapy* 21(2):282-290.
Bevan, A.K. et al. (Nov. 2011, e-pub. Aug. 2, 2011). "Systemic Gene Delivery in Large Species for Targeting Spinal Cord, Brain, and Peripheral Tissues for Pediatric Disorders," *Mol. Ther.* 19:1971-1980.
Bossis, I. et al. (Jun. 2003). "Cloning of an Avian Adeno-Associated Virus (AAAV) and Generation of Recombinant AAAV Particles," *J. Virol.* 77(12):6799-6810.
Boutin, S. et al. (Jun. 2010, e-pub. Apr. 28, 2010). "Prevalence of Serum IgG and Neutralizing Factors Against Adeno-Associated Virus (AAV) Types 1, 2, 5, 6, 8, and 9 in the Healthy Population: Implications for Gene Therapy Using AAV Vectors," *Hum. Gene Ther.* 21:704-712.
Bowerman, M. et al. (2012). "A Critical smn Threshold in Mice Dictates Onset of an Intermediate Spinal Muscular Atrophy Phenotype Associated with a Distinct Neuromuscular Junction Pathology," *Neuromuscul. Disord.* 22:263-276.

(Continued)

*Primary Examiner* — James D Schultz
(74) *Attorney, Agent, or Firm* — Morrison & Foerster LLP

(57) ABSTRACT

The present provides methods for treating spinal muscular atrophy using a self-complementary recombinant adeno-associated virus (rAAV) viral particle comprising a transgene expressing SMN. In one aspect, the viral particles are administered the spinal column or cisterna magna in a human subject; for example, a pediatric human subject. Viral particles comprising AAV9 capsids are contemplated.

19 Claims, 17 Drawing Sheets
Specification includes a Sequence Listing.

(56) References Cited

OTHER PUBLICATIONS

Butchbach, M.E. R. et al. (2010). "Effects of 2,4-diaminoquinazoline Derivatives on SMN Expression and Phenotype in a Mouse Model for Spinal Muscular Atrophy," *Hum. Mol. Genet.* 19(3):454-467.
Chen, S. et al. (Apr. 1994). "Gene Therapy for Brain Tumors: Regression of Experimental Gliomas by Adenovirus-Mediated Gene Transfer in vivo," *PNAS* 91:3054-3057.
Chen, T.-H. et al. (Dec. 14, 2010). Randomized, Double-Blind, Placebo-Controlled Trial of Hydroxyurea in Spinal Muscular Atrophy, *Neurology* 75:2190-2197.
Clark, K.R. et al. (Apr. 10, 1999). "Highly Purified Recombinant Adeno-Associated Virus Vectors Are Biologically Active and Free of Detectable Helper and Wild-Type Viruses," *Hum. Gene Ther.* 10(6):1031-1039.
Coovert, D.D. et al. (1997). "The Survival Motor Neuron Protein in Spinal Muscular Atrophy" *Hum Mol. Genet* 6(8):1205-1214.
Davidson, B.L. et al. (Mar. 28, 2000). "Recombinant Adeno-Associated Virus Type 2, 4, and 5 Vectors: Transduction of Variant Cell Types and Regions in the Mammalian Central Nervous System," *PNAS* 97(7):3428-3432.
Dominguez, E. et al. (2011, e-pub. Nov. 30, 2010). "Intravenous scAAV9 Delivery of a Codon-Optimized SMN1 Sequence Rescues SMA Mice," *Hum. Mol. Genet.* 20(4):681-693.
Duque, S. (Jul. 2009). "Intravenous Administration of Self-Complementary AAV9 Enables Transgene Delivery to Adult Motor Neurons," *Mol. Ther.* 17(7):1187-1196.
Fallini, C. et al. (Jun. 26, 2012, e-pub Jan. 28, 2012). "Spinal Muscular Atrophy: The Role of SMN in Axonal mRNA Regulation," *Brain Res.* 1462:81-92, 19 pages.
Farooq, F. et al. (Aug. 2011). "Prolactin Increases SMN Expression and Survival in a Mouse Model of Severe Spinal Muscular Atrophy Via The STAT5 Pathway," *J. Clin. Invest.* 121(8):3042-3050.
Federici, T. et al. (2012, e-pub Sep. 15, 2011). "Robust Spinal Motor Neuron Transduction Following Intrathecal Delivery of AA V9 pigs," *Gene Ther.* 19:852-859.
Fisher, K.J. et al. (Jan. 1996). "Transduction with Recombinant Adeno-Associated Virus for Gene Therapy is Limited by Leading-Strand Synthesis," *J. Virol.* 70(1):520-532.
Foust, K.D. et al. (Mar. 2010). "Rescue of the Spinal Muscular Atrophy Phenotype in a Mouse Model by Early Postnatal Delivery of SMN," *Nat. Biotech.* 28(3):271-274, 11 pages.
Gao, G. et al. (Sep. 3, 2002). "Novel Adeno-Associated Viruses from Rhesus Monkeys as Vectors for Human Gene Therapy," *PNAS,* 99(18):11854-11859.
Gao, G. et al. (May 13, 2003). "Adeno-Associated Viruses Undergo Substantial Evolution in Primates During Natural Infections," *PNAS* 100(10):6081-6086.
Gao, G. et al. (Jun. 2004). "Clades of Adeno-Associated Viruses are Widely Disseminated in Human Tissues," *J. Virol.* 78(12):6381-63878.
Garbes, L. et al. (Jul. 7, 2009). "LBH589 Induces up to 10-Fold SMN Protein Levels by Several Independent Mechanisms and is Effective Even in Cells From SMA Patients Non-Responsive to Valproate," *Hum Mol Genet.* 18(19):3645-3658.
Glascock, J.J. et al. (Jan. 6, 2012). "Direct central nervous system delivery provides enhanced protection following vector mediated gene replacement in a severe model of Spinal Muscular Atrophy," *Biochemical and Biophysical Research Communications* 417(1):376-381, 11 pages.
Glascock, J.J. et al. (Mar. 2012). "Decreasing Disease Severity in Symptomatic, SMN–/–;SMN2+/+, Spinal Muscular Atrophy Mice Following scAAV9-SMN Delivery," *Human Gene Therapy* 23(3):330-335.
Gray S.J. (Apr. 2013). "Global CNS Gene Delivery and Evasion of Anti-AAV Neutralizing Antibodies by Intrathecal AAV Administration in Non-Human Primates," *Gene Therapy* 20(4)450-459.
Gray, S.J. et al. (Jun. 2011, e-pub Apr. 12, 2011). "Preclinical Differences of Intravascular AAV9 Delivery to Neurons and Glia: a Comparative Study of Adult Mice and Nonhuman Primates," *Mol. Ther.* 19(6):1058-1069.

Guo, Z.S. et al. (1996). "Evaluation of Promoter Strength for Hepatic Gene Expression in vivo Following Adenovirus-Mediated Gene Transfer," *Gene Ther.* 3(9):802-810.
Hamilton, G. et al. (Jan. 2013). "Spinal Muscular Atrophy: Going Beyond the Motor Neuron," *Trends Mol. Med.* 19(1):40-50.
Heier, C.R. et al. (2009, Jan. 15, 2009). "Translational Readthrough by the Aminoglycoside Geneticin (G418) Modulated SMN Stability in vitro and Improves Motor Function in SMA Mice in vivo," *Hum. Mol. Genet.* 18(7):1310-1322.
Hua, Y. et al. (2010, e-pub. Jul. 12, 2010). "Antisense Correction of SMN2 Splicing in the CNS Rescues Necrosis in a Type III SMA Mouse Model," *Genes Dev.* 24:1634-1644.
Hua, Y. et al. (Apr. 2008). "Antisense masking of an hnRNP A1/A2 intronic splicing silencer corrects SMN2 splicing in transgenic mice," *Am. J. Hum. Genet.* 82:834-848.
Hua, Y. et al. (Oct. 5, 2011). "Peripheral SMN Restoration is Essential for Long-Term Rescue of a Severe Spinal Muscular Atrophy Mouse Model," *Nature* 478:123-126, 11 pages.
International Search Report dated Aug. 13, 2013, for PCT Application No. PCT/US2013/039163, filed on May 1, 2013, 8 pages.
Kim, D.W. et al. (Jul. 1990). "Use of the Human Elongation Factor 1 Alpha Promoter As a Versatile and Efficient Expression System," *Gene* 91(2):217-23.
Kolb, S.J. et al. (Aug. 2011, e-pub. Apr. 11, 2011). "Spinal Muscular Atrophy: A Timely Review," *Arch. Neurol.* 68(8):979-984.
Kole, R. et al. (Feb. 2012, e-pub. Jan. 20, 2012). "RNA Therapeutics: Beyond RNA Interference and Antisense Oligonucleotides," *Nature Rev. Drug Dis.* 11:125-140.
Kotin, R.M. et al. (Jul. 1994). "Prospects for the Use of Adeno-Associated Virus as a Vector for Human Gene Therapy," *Hum. Gene Ther.* 5(7):793-801.
Le, T.T. et al. (2005) "SMNΔ7, The Major Product of the Centromeric Survival Motor Neuron (SMN2) Gene, Extends Survival in Mice with Spinal Muscular Atrophy and Associates with Full-length SMN," *Hum Mol. Genet.* 14(6):845-857.
Lefebvre, S. et al. (Jan. 13, 1995). "Identification and Characterization of a Spinal Muscular Atrophy-determining Gene," *Cell* 80(1):155-165.
Lewelt, A. et al. (Feb. 2012). "New therapeutic approaches to spinal muscular atrophy," *Curr. Neurol. Neurosci. Rep.* 12(1):42-53, 17 pages.
Lorson, M.A. et al. (Dec. 2011, e-pub. Feb. 25, 2011). "Disruption of the survival motor neuron (SMN) gene in pigs using ssDNA," *Transgenic Res.* 20(6):1293-1304.
Markowitz, J.A. et al. (2012). "Spinal Muscular Atrophy: A Clinical and Research Update," *Ped. Neurol.* 46:1-12.
Mattis, V.B. et al. (2009). "Delivery of a Read-Through Inducing Compound, TC007, Lessens the Severity of a Spinal Muscular Atrophy Animal Model," *Hum. Mol. Genet.* 18(20):3906-3913.
McLaughlin, S.K. et al. (Jun. 1988). "Adeno-Associated Virus General Transduction Vectors: Analysis of Proviral Structures," *J. Virol.* 62:1963-1973.
Mercuri, E. et al (Jan. 2, 2007, e-pub. Nov. 2, 2006). "Randomized, double blind, placebo-controlled trial of phenylbutyrate in spinal muscular atrophy," *Neurology* 68(1):51-55.
Monani, U.R. et al. (1999). "A Single Nucleotide Difference that Alters Splicing Patterns Distinguishes the SMA gene *SMN1* from the Copy Gene *SMN2*," *Hum. Mol. Genet.* 8(7):1177-1183.
Nathwani, A.C. et al. (Dec. 22, 2011). "Adenovirus-associated virus vector-mediated gene transfer in hemophilia B," *N. Engl. J. Med.* 365(25):2357-2365.
Niwa, H. et al. (Dec. 1991). "Efficient Selection for High-Expression Transfectants with a Novel Eukaryotic Vector," *Gene.* 108(2):193-199.
Passini M.A. et al. (Jun. 2003). "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of β-Glucuronidase-Deficient Mice," *J. Viral.* 77(12):7034-40.
Passini, M.A. et al. (Apr. 2010). "CNS-Targeted Gene Therapy Improves Survival and Motor Function in a Mouse Model of Spinal Muscular Atrophy," *J. Clin. Invest.* 120(4):1253-1264.

(56) References Cited

OTHER PUBLICATIONS

Passini, M.A. et al. (Mar. 2, 2011). "Antisense oligonucleotides delivered to the mouse CNS ameliorate symptoms of severe spinal muscular atrophy," *Sci. Transl. Med.* 3(72):72ra18, 12 pages.

Passini, M.A. et al. (May 17, 2011a, e-pub. Feb. 19, 2011). "Prospects for the Gene Therapy of Spinal Muscular Atrophy" *Trends Mol. Med.* 17(5):259-265.

Pechan, P. et al. (Jan. 2009). "Novel anti-VEGF Chimeric Molecules Delivered by AAV Vectors for Inhibition of Retinal Neovascularization," *Gene Ther.* 16(1):10-16.

Rochette, C.F. et al. (2001, e-pub. Mar. 2, 2001). "*SMN* Gene Duplication and the Emergence of the *SMN2* Gene Occurred in Distinct Hominids: *SMN2* Is Unique to *Homo sapiens*" *Human Genetics* 108(3):255-266.

Samaranch, L. et al. (Apr. 2012, Dec. 27, 2011). "Adeno-Associated Virus Serotype 9 Transduction in the Central Nervous System of Nonhuman Primates," *Hum. Gene Ther.* 23:382-389.

Shababi, M. et al. (May 2012, e-pub Jan. 17, 2012). "Partial Restoration of Cardio-Vascular Defects in Rescued Severe Model of Spinal Muscular Atrophy," *Journal of Molecular and Cellular Cardiology* 52(5):1074-1082, 18 pages.

Singh, N.K. et al. (Feb. 2006). Splicing of a Critical Exon of Human *Survival Motor Neuron* is Regulated by a Unique Silencer Element Located in the Last Intron, *Mol. Cell. Biol.* 26(4):1333-1346.

Sumner, C.J. et al. (Nov. 2003). "Valproic Acid Increases SMN Levels in Spinal Muscular Atrophy Patient Cells," *Ann. Neurol.* 54(5):647-654.

Treleaven, C.M. (Sep. 2012). "Gene Transfer to the CNS is Efficacious in Immune-Primed Mice Harboring Physiologically Relevant Titers of Anti-AAV Antibodies," *Mol. Ther.* 20(9):1713-1723.

Valori, C.F. (Jun. 9, 2010). "Systemic Delivery of scAAV9 Expressing SMN Prolongs Survival in a Model of Spinal Muscular Atrophy," *Sci Transl Med.* 2(35ra42):9 pages.

Veldwijk, M.R. et al. (Aug. 2002). "Development and Optimization of a Real-Time Quantitative PCR-Based Method for the Titration of AAV-2 Vector Stocks," *Mol. Ther.* 6(2):272-278.

Wang, Z. et al. (2003). "Rapid and Highly Efficient Transduction by Doouble Stranded Adeno-Associated Virus Vectors in vitro and in vivo," *Gene. Ther.* 10:2105-2111.

Written Opinion dated Aug. 13, 2013, for PCT Application No. PCT/US2013/039163, filed on May 1, 2013, 5 pages.

Xiao, X. et al. (1997). "Gene Transfer by Adeno-Associated Virus Vectors in the Central Nervous System," *Exp. Neurobiol.* 144:113-124.

Bu, J. et al. (May 2012). "Identifying Motor Neuron Transduction Efficiencies that are Efficacious in SMA Mice and Achievable by Intrathecal Delivery in a Large Animal Model," *Molecular Therapy* 20(1):S31, No. 76, 1 page.

Ohno, K. et al. (Jun. 14, 2019, e-pub. Dec. 8, 2018). "Kinetics and MR-Based Monitoring of AAV9 Vector Delivery Into Cerebrospinal Fluid of Nonhuman Primates," Mol Ther Methods Clin Dev. 13:47-54.

U.S. Appl. No. 16/449,221, filed Jun. 21, 2019 by Passini et al. (U.S. Patent Application is not submitted herewith pursuant to the waiver of 37 C.F.R. § 1.98(a)(2)(iii) issued by the Office dated Sep. 21, 2004).

U.S. Appl. No. 16/794,031, filed Feb. 18, 2020 by Passini et al. (U.S. Patent Application is not submitted herewith pursuant to the waiver of 37 C.F.R. § 1.98(a)(2)(iii) issued by the Office dated Sep. 21, 2004).

Figure 1

MAMSSGGGSGGGVPEQEDSVLFRRGTGQSDDSDIWDDTALIKAYDKAVASFKHALKNGDICETS
GKPKTTPKRKPAKKNKSQKKNTAASLQQWKVGDKCSAIWSEDGCIYPATIASIDFKRETCVVVYT
GYGNREEQNLSDLLSPICEVANNIEQNAQENENESQVSTDESENSRSPGNKSDNIKPKSAPWN
SFLPPPPPMPGPRLGPGKPGLKFNGPPPPPPPHLLSCWLPPFSGPPIPPPPPICPDSLDD
ADALGSMLISWYMSGYHTGYYMGFRQNQKEGRCSHSLN (SEQ ID NO:1)

Figure 2 atggcgatgagcagcggcggcagtggtggcggcgtccggagcaggaggattccgtcgttccggcgcggcacaggccagagcg
atgattctgacatttggatgatacagcactgataaagcatatgataaagctgtggcttcatttaagcatgtctaaagaatggtgacattt
gtgaaacttcgggtaaaccaaaagaaccacactcaaaagaagaataaaagccaaaagaagaatactgcagcttc
cttacaacagtggaaagttggggacaaatgttctgccatttggtcagaagacggttgcatttaccagctaccattgcttcaattgatttaag
agagaaacctgtgtttgtttacactgatatggaaatagagagaggagcaaaatctgtccgatctactttcccaatctgtgaagtagcta
ataatatagaacagaatgtcaagagaatgaaatgaaagccaagtttcaacagatgaagtgagaactccaggtctcctggaaata
aatcagataacatcaagcccaaatctgtccatggaactcttttctccctccaccacccccatgccaggccagagactggaccagga
aagccaggtctaaattcaatgcccaccacgccacctccatatgtccagattctcttgatgatgctttgggaagtattaattcatggtacatgagt
gaccaccaataattcccccaccacttccccatgtccagattctcttgatgatgctttgggaagtattaattcatggtacatgagt
ggctatcatactggctattatatggtttcagacaaaatcaaaagaagaaggaaggtgctcacattccttaaattaa (SEQ ID NO:2)

Figure 3 atggctatgagcagtggcggctctggcggcggagtgcctgagcaggaagatagcgtgctgttcagacggggcaccggccagagcga cgacagcgacatctggatgacgacccgccctgatcaaggcctacgacacaaggccgtgccagcttcaagcacgccctgaagaacggc gatatctgcgagacaagcgcaagcccaagagaaagcccgccaagagaacaagagagcagagaagaata ccgccgcctccctgcagcagtggaagtggcgataagtgcagcgccatttggagcgaggacgctgcatctacccgccacaatcg ccagcatcgacttcaagcggaaacctgctggtgtgtacacaggctacggcaacagagaggaacaagaacctgagcgacctgctg agcccatctgcgaggtggccaacaacatcgagcagaacgccaggaaacgccagaaaacgagaacgagtccagtgtccacgacgagag cgagaacagagaagcccggcaacaagagcgacaacatcaagcctaagagagcgcccctgaacagttcctgctgcctcccctcca ccaatgcctggcctagactggacctggcaagcccggcctgaagttcaatggccctctcccactccaccaccccctcatct gctgagctgttggctgccccatccctagcggccctccatcattcctccaccccccaatctgccccgacagcctgatgatgctgat gccctggctccatgctgatctcttggtacatgagcgctaccacaccggctactacatggcttccggcagaaccagaaagagggcc gctgtagccacagcctgaactga (SEQ ID NO:3)

Figure 4 atggcgatgagcagcggtggttccggaggaggggtgccggagcaggaggattccgtccttcagacggggaaccggccagtcgga cgactcggacatctggatgacaccgcactgatgatcaaagcatacgataaagcatgtgcatcgttcaagcacgcccttaagaatggaga catttgcgaaccagcggaagccaaaaactactccgaagcgcaagcccgccaagagaataagtcacagaagaaaacaccg ccgcttcgctgcaacagtgggacaagtgctccgcgatctgtcagagatgctgcatctaccggccacgatcgcctc catcgacttcaagcggaaacttgtgtgtctacactggctacggaaaccgcgaggaacagaatcagcgaatcctcagcccg atttgtgaggtggccaacatatcgaacagaacgcgcaagaaaacgagaacgagtccaagtgtgacgaatcggaaaattc gcgctcaccaggaaaacaagtcagataacatcaagcccggactcaaattcaacgccacgcctccgccactcctccacctgctgtcctg accgaggctggaccgggaaagccgggactcaaattcaacgggactcaaattcaacgccacgcctccgccactcctccacctgctgtcctg ctggctgccgccatttccgtcggtccgcctatcatcctccaccgccgactcactcgacgatgtgacgccctggggt caatgctgatctcctggtatatgtccggctaccatacccggatactacatggattccggcagaaccaaaaggaaggagatgctccatt cgctgaattga (SEQ ID NO:4)

```
   1 GGGCACTCCC TCTCTGCGCG CTCGCTCGCT CACTGAGGCC GGGCGACCAA AGGTCGCCCG ACGCCCGGGC TTTGCCCGGG CGGCCTCAGT GAGCGAGCGA
                     AAV ITR A                                                              AAV ITR B
 101 GCGGGCAGAG AGGGAGTGGC CAACTCCATC ACTAGGGGTT CCTGCGGCCT CTAGAGGATC TGCGATCGCT GTCGTCGGGG AGTCGTTTAA AGTAATCAAT
                     AAV ITR D                                AAV Sequence                              CMV enhancer
 201 TACGGGGTCA TTAGTTCATA GCCCATATAT GGAGTTCCGC GTTACATAAC TTACGGTAAA TGGCCCGCCT GGCTGACCGC CCAACGACCC CCGCCCATTG
                                                                    CMV enhancer
 301 ACGTCAATAA TGACGTATGT TCCCATAGTA ACGCCAATAG GGACTTTCCA TTGACGTCAA TGGGTGGACT ATTTACGGTA AACTGCCCAC TTGGCAGTAC
                                                                    CMV enhancer
 401 ATCAAGTGTA TCATATGCCA AGTACGCCCC CTATTGACGT CAATGACGGT AAATGGCCCG CCTGGCATTA TGCCCAGTAC ATGACCTTAT GGGACTTTCC
                     CMV enhancer                                                              CBA promoter
 501 TACTTGGCAG TACATCTACG TATTAGTCAT CGCTATTACC ATGGTCGAGG TGAGCCCCAC GTTCTGCTTC ACTCTCCCCA TCTCCCCCCC CTCCCCACCC
                                                                    CBA promoter
 601 CCAATTTTGT ATTTATTTAT TTTTTAATTA TTTTGTGCAG CGATGGGGGC GGGGGGGGGG GGGGGGCGCG CGCCAGGCGG GGCGGGGCGG GGCGAGGGGC
                                                                    CBA promoter
 701 GGGGCGGGGC GAGGCGGAGA GGTGCGGCGG CAGCCAATCA GAGCGGCGCG CTCCGAAAGT TTCCTTTTAT GGCGAGGCGG CGGCGGCGGC GGCCCTATAA
                                                                    Exon 1
                                                                    Chimeric intron: CBA
 801 AAACGGAGC GCGCGTGGCGG CGCGCGGTGA GTGGCGCGGA CGGCCCGAGT TGCGACGCGC CCTTCGCCCC CGTGCCCCGC CTCGACTGAC TCTGACTGAC
                                                                    Chimeric intron: CBA
 901 CGGGTTACTC CCAGAGTGA AAGGGCTCCG GGACTAGAGG GCGGGGCGGA CGGCCCCTTCT GTAATTAGG CTTGGTTTAAA TGACGGCTTG TTCTTTTCT GTGGCTGCGT
                                                                    Chimeric intron: Rabbit b-globin
1001 GAAAGCCTTG ACGGTTACTC CCAGAGTGA GCGGGGCTCCG GGACTAGAGG GCGGGGCGGA CGGCCCCTTCT GTAATTAGG CTTGGTTTAAA TGACGGCTTG TTCTTTTCT GTGGCTGCGT
                                                                    Chimeric intron: Rabbit b-globin
1101 GTCTCATCAT TTTGGCAAAG AATTTTGGAA CTCGAATTCA TGGCGATGAG CAGCGGCGGC AGCGGTGGCG GCGTCCGGGA GCAGGAGGAT TCCGTGCTGT
                                                                    Human SMN1
1201 TCCGGGCGGG CACAGGCCAG AGCGATGATT CTGACATTTG GGATGATACA GCACTGAGGA AAGCTGGCAA TAAAGCTCTG GCTTCATTTA AGCATGCTCT
                                                                    Human SMN1
```

Figure 8 (continued)

```
1301  AAAGATGCT GACATTTGTG AAACTTCGGG TAAACCAAAA ACCACACCTA AAAGAAAACC TGCTAAGAGA AATAAAAGCC AAAAGAAGAA TACTGTGAGCT
         Human SMN1
1401  TCCTTACAC AGTGGAAAGT TGGGACAAA TGTTCTGCCA TTTATTGAAA AGACGGTTGG ATTACTCCAG CTACCATTGC TTCAATTGAT TTTAAGAGAG
         Human SMN1
1501  AAACCTGTGT TGTGGTTTAC ACTGGATATG GAAATAGAGA GGAGCAAAAT CTGTCCGATC TACTTTCCCC AATCTGTGAA GTAGCTAATA ATATAGACAA
         Human SMN1
1601  GAATGCTCAA GAGAATGAAA ATGAAAGCCA AGTTTCAACA GATGAAAGTG AGAACTCGAG ATGTCCTGGA AATAAATGAG ATAACATCAA GCCCAAATCT
         Human SMN1
1701  GCTCCATGGA ACTCTTTTCT CCCTCCACCA CCCCCCATGC CAGGGCCAAG ACTGGGACCA GGAAAGCCAG GTCTAAAATT CAATGCCCCA CCACCGCCAC
         Human SMN1
1801  CGCCACCACC ACCACCCCAC TTACTATCAT GCTGGCTGCC TCCATTTCCT TCTGGACCAC CAATAATTCC CCCACCACCT CCCATATGTC CAGATTCTCT
         Human SMN1
1901  TGATGATGCT GATGCTTTGG GAAGTATGTT AATTTCATGG TACATTAGTG TAAGAAATGG CCTCCATCTT CCCTGGTTCT AATAAGCCATA AAAGAAGGA
         Human SMN1                                                                              BGH pA
2001  AGGTGCTCAC ATTCCTTAAA TTAAGGAGTA CACTGCCTTG CCCTGATAGC CCTGTGCCTT CTAGTTGCCA GCCATCTGTT GTTTGCCCCT CCCCCGTGCC
                                                                      BGH pA
2101  TTCCTTGACC CTGGAAGGTG CCACTCCCAC TGTCCTTTCC TAATAAAATG AGGAAATTGC ATCGCATTGT CTGAGTAGGT GTCATTCTAT TCTGGGGGGT
                          BGH pA                                                                AAV2 ITR B
2201  GGGGTGGGGC AGGACAGCAA GGGGGAGGAT TGGGAAGACA ATAGCAGGCA TGCTGGGGAT GCGGTGGGCT CTATGGCTTC TGAGGCGGAA
           AAV2 ITR C                                      AAV2 ITR A
2301  CGAGCAAAAGG TGGCCCAGG CCCGGGCTTT GCCCGGGCGG
        AAV2 ITR D
```

COMPOSITIONS AND METHODS FOR TREATING SPINAL MUSCULAR ATROPHY

CROSS-REFERENCE TO RELATED APPLICATIONS

This application is a National Phase application under 35 U.S.C. § 371 of International Application No. PCT/US2013/039163 filed May 1, 2013, the disclosures of which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 159792009900 SeqList.txt, date recorded: Oct. 29, 2015, size: 11,883 KB).

FIELD OF THE INVENTION

The present invention relates to AAV vectors and methods of using AAV vectors for treating spinal muscular atrophy.

BACKGROUND OF THE INVENTION

Spinal muscular atrophy (SMA) is an autosomal recessive neuromuscular disorder caused by mutations in the survival motor neuron 1 (SMN1) gene. Resultant deficiency in the encoded 294-amino acid SMN protein leads to presentation of a spectrum of disease characteristics. These include progressive muscular weakness and atrophy, respiratory insufficiency and premature death resulting from the degeneration of motor neurons in the spinal cord. Disease severity is inversely correlated with the copy number of a paralogue gene, SMN2, by virtue of the ability of this ancillary gene to direct the production of approximately 10-20% functional SMN.

Based on the current understanding for the underlying molecular basis of the disease, a number of therapeutic strategies aimed at increasing the levels of functional SMN in the more disease-prone cells are being considered.

However, despite the development of these therapeutic strategies, successful translation of these concepts to clinical efficacy has remained difficult. Therefore, there is a need for developing further compositions and methods to treat spinal muscular atrophy in human patients.

BRIEF SUMMARY OF THE INVENTION

In some aspects, the invention provides methods for treating spinal muscular atrophy in a primate, comprising administering to the spinal cord and/or cisterna magna of the primate at least $1 \times 10^{12}$ genome copies of a recombinant adeno-associated virus (rAAV) viral particle comprising a vector encoding a primate SMN.

In some aspects, the invention provides methods for ameliorating a symptom of spinal muscular atrophy in a primate, comprising administering to the spinal cord and/or cisterna magna of the primate at least $1 \times 10^{12}$ genome copies of a recombinant adeno-associated virus (rAAV) viral particle comprising a vector encoding a primate SMN. In some embodiments, the symptom of spinal muscular atrophy is one or more of muscle wasting, inability to achieve motor milestones, inability to sit, inability to walk, paralysis, respiratory dysfunction, bulbar dysfunction, motor neuron cell loss and neuromuscular junction pathology.

In some aspects, the invention provides methods for delivering a heterologous transgene encoding a primate SMN in a motor neuron in a primate, comprising administering to the spinal cord and/or cisterna magna of the primate at least $1 \times 10^{12}$ genome copies of a recombinant adeno-associated virus (rAAV) viral particle comprising a vector encoding a primate SMN.

In some embodiments of the above aspects, at least 10-30% of the motor neurons in the lumbar, thoracic and cervical regions of the spinal cord are transduced. In some embodiments, more than about any of 5%, 10%, 15%, 20%, 25%, 30%, 35%, 40%, 45%, 50%, 55%, 60%, 65%, 70%, 75% or 100% of motor neurons throughout the spinal cord are transduced. In some embodiments, at least 30% of SMN wild type levels are generated throughout the spinal cord. In some embodiments of the invention, administration to the spinal cord and/or cisterna magna of an AAV viral particle comprising a transgene encoding a primate SMN results in expression of at least about any of 20%, 25%, 30%, 35%, 40%, 45%, 50%, 55%, 60%, 65%, 70%, 75%, 80%, 85%, 90%, 95% or 100% of levels of SMN expression in a normal individual.

In some embodiments of the above aspects, the rAAV is administered via direct injection into the spinal cord, via intrathecal injection, or via intracisternal injection. In some embodiments, the rAAV is administered to more than one location of the spinal cord or cisterna magna. In some embodiments, the rAAV is administered to more than one location of the spinal cord. In some embodiments, the rAAV is administered to one or more of a lumbar subarachnoid space, thoracic subarachnoid space and a cervical subarachnoid space of the spinal cord. In some embodiments, the rAAV is administered to the cisterna magna. In some embodiments, multiple injections of the rAAV are simultaneous or sequential. In some embodiments, sequential injections are within one, two, three, six, nine, twelve or 24 hours of each other.

In some embodiments of the above aspects, at least $3.5 \times 10^{11}$ genome copies per kg body weight of rAAV is administered to the primate. In further embodiments, at least $3.5 \times 10^{12}$ genome copies per kg body weight of rAAV is administered to the primate. In some embodiments, at least $5 \times 10^{12}$ genome copies per kg body weight of rAAV is administered to the primate. In further embodiments, at least $5 \times 10^{13}$ genome copies per kg body weight of AAV is administered to the primate. In some embodiments, at least $2.5 \times 10^{12}$ genome copies are administered to the primate. In other embodiments, at least $1.25 \times 10^{13}$ genome copies are administered to the primate.

In some embodiments of the above aspects, the AAV viral particle comprises an AAV1, AAV2, AAV3, AAV4, AAV5, AAV6, AAV7, AAV8, AAVrh8, AAV9, AAV10, AAVrh10, AAV11, or AAV12 serotype capsid. In further embodiments, the rAAV viral particle comprises an AAV serotype 9 capsid. In some embodiments, the rAAV viral particle comprises an AAV serotype capsid from Clades A-F.

In some embodiments of the above aspects, the vector comprises AAV1, AAV2, AAV3, AAV4, AAV5, AAV6, AAV7, AAV8, AAVrh8, AAV9, AAV10, AAVrh10, AAV11, or AAV12 serotype inverted terminal repeats (ITRs). In further embodiments, the vector comprises AAV serotype 2 ITRs. In other embodiments, the rAAV viral particle comprises an AAV serotype capsid from Clades A-F. In further embodiments, the ITR and the capsid are derived from the same AAV serotype. In other embodiments, the ITR and the capsid are derived from different AAV serotypes. In some embodiments of the invention, the rAAV viral particle comprises an AAV-9 capsid, and wherein the vector comprises AAV2 ITRs.

In some embodiments of the above aspects, the vector is a self-complimenting vector. In some embodiments, the vector comprises a first heterologous polynucleotide sequence encoding a SMN-1 transgene and a second heterologous polynucleotide sequence encoding a complement of the SMN-1 transgene, wherein the first heterologous polynucleotide sequence can form intrastrand base pairs with the second polynucleotide sequence along most or all of its length. In further embodiments, the first heterologous polynucleotide sequence and the second heterologous polynucleotide sequence are linked by a mutated AAV ITR, wherein the mutated AAV ITR comprises a deletion of the D region and comprises a mutation of the terminal resolution sequence.

In some embodiments of the above aspects, the SMN-1 transgene is operably linked to a promoter. In further embodiments, the promoter is capable of expressing the SMN-1 transgene in neurons of the spinal cord. In other embodiments, the promoter is capable of expressing the SMN-1 transgene in motor neurons of the spinal cord. In yet further embodiments, the promoter comprises a human β-glucuronidase promoter or a cytomegalovirus enhancer linked to a chicken β-actin promoter.

In some embodiments of the above aspects, the SMN-1 transgene is a human SMN-1 transgene. In further embodiments, the SMN comprises the amino acid sequence of SEQ ID NO:1. In further embodiments, the vector comprises a polynucleotide encoding the amino acid sequence of SEQ ID NO:1. In other embodiments, the polynucleotide comprises the nucleic acid sequence of SEQ ID NO:2, SEQ ID NO:3 or SEQ ID NO:4. In other embodiments, the AAV viral particle comprises a recombinant viral genome derived from the polynucleotide of SEQ ID NO:5 or SEQ ID NO:6.

In some embodiments of the above aspects, the primate is a human. In further embodiments, the human is a pediatric subject. In other embodiments, the human is a young adult. In some embodiments, the human has spinal muscular atrophy. In some embodiments, the primate has a mutation in the endogenous SMN-1 gene. In some embodiments, the primate has a partial deletion of the endogenous SMN1 gene. In some embodiments, the primate has a complete deletion of the endogenous SMN-1 gene. In some embodiments, the expression of the mutant SMN-1 gene in spinal cord or brain of the primate is deficient compared to expression of SMN-1 in a primate with a wild-type SMN-1 gene.

In some embodiments of the above aspects, the rAAV viral particle is in a pharmaceutical composition. In some embodiments, the pharmaceutical composition further comprises a pharmaceutically acceptable carrier.

It is to be understood that one, some, or all of the properties of the various embodiments described herein may be combined to form other embodiments of the present invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

BRIEF DESCRIPTION OF THE DRAWINGS

FIG. 1 shows the amino acid sequence of SMN protein (SEQ ID NO:1).

FIG. 2 shows a non-optimized nucleic acid sequence of hSMN1 (SEQ ID NO:2).

FIG. 3 shows an optimized nucleic acid sequence of hSMN1 (SEQ ID NO:3).

FIG. 4 shows an optimized nucleic acid sequence of hSMN1 (SEQ ID NO:4).

FIG. 6 shows the nucleic acid sequence for pscAAV-GUSB hSMN1 (SEQ ID NO:5).

FIG. 8 shows the nucleic acid sequence for pscAAV-minCBA hSMN1 (SEQ ID NO:6).

DETAILED DESCRIPTION

Figure 5:
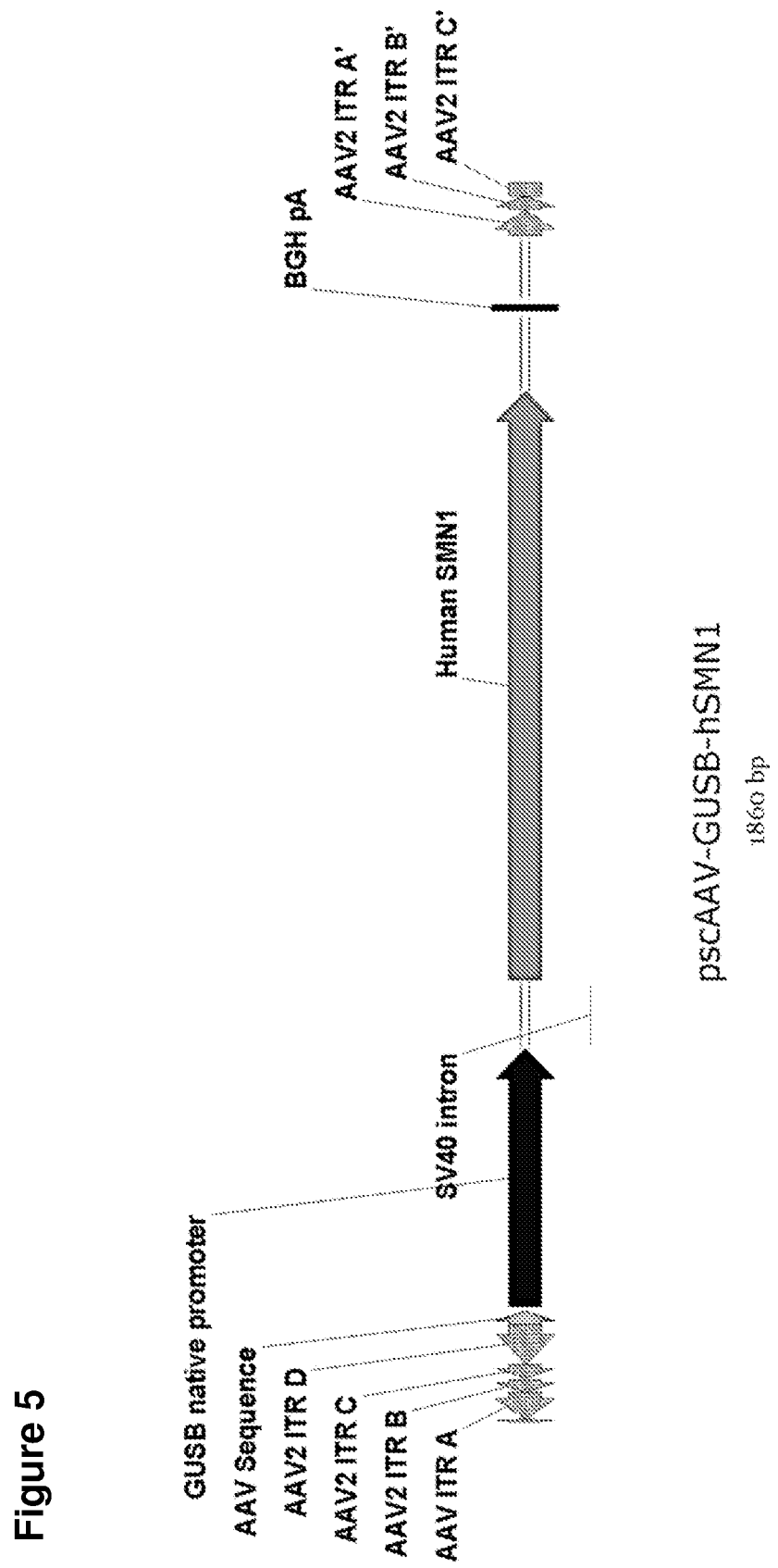
FIG. 5 shows a plasmid map of pscAAV-GUSB hSMN1.

The present invention provides, inter alia, compositions and methods for treating spinal muscular atrophy in a subject. The methods comprise delivering of a recombinant adeno-associated virus (rAAV) vector encoding SMN into the spinal cord and/or cisterna magna (e.g., intrathecal delivery). In some embodiments of the invention, the AAV vector is a self-complementing vector for efficient expression of the therapeutic transgene. In some aspects, the methods ameliorate one or more symptoms of spinal muscular atrophy including but not limited to muscle wasting, paralysis, respiratory dysfunction, motor neuron cell loss and neuromuscular junction pathology.

I. General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4$^{th}$ ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6$^{th}$ ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 2011).

II. Definitions

A "vector," as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P—NH$_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one, preferably two, inverted terminal repeat sequences (ITRs).

A "recombinant AAV vector (rAAV vector)" refers to a polynucleotide vector comprising one or more heterologous sequences (i.e., nucleic acid sequence not of AAV origin) that are flanked by at least one, preferably two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g., in a chromosome or in another vector such as a plasmid used for cloning or transfection), then the rAAV vector may be referred to as a "pro-vector" which can be "rescued" by replication and encapsidation in the presence of AAV packaging functions and suitable helper functions. An rAAV vector can be in any of a number of forms, including, but not limited to, plasmids, linear artificial chromosomes, complexed with lipids, encapsulated within liposomes, and, most preferable, encapsidated in a viral particle, particularly an AAV particle. A rAAV vector can be packaged into an AAV virus capsid to generate a "recombinant adeno-associated viral particle (rAAV particle)".

"Heterologous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector, is a heterologous nucleotide sequence with respect to the vector.

The term "transgene" refers to a polynucleotide that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome. In another aspect, it may be transcribed into a molecule that mediates RNA interference, such as siRNA.

The terms "genome particles (gp)," "genome equivalents," or "genome copies" as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) *Hum. Gene Ther.*, 10:1031-1039; Veldwijk et al. (2002) *Mol. Ther.*, 6:272-278.

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) *J. Virol.*, 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) *Exp. Neurobiol.*, 144:113-124; or in Fisher et al. (1996) *J. Virol.*, 70:520-532 (LFU assay).

An "inverted terminal repeat" or "ITR" sequence is a term well understood in the art and refers to relatively short sequences found at the termini of viral genomes which are in opposite orientation.

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C' and D regions), allowing intrastrand base-pairing to occur within this portion of the ITR.

A "terminal resolution sequence" or "trs" is a sequence in the D region of the AAV ITR that is cleaved by AAV rep proteins during viral DNA replication. A mutant terminal resolution sequence is refractory to cleavage by AAV rep proteins.

A "helper virus" for AAV refers to a virus that allows AAV (which is a defective parvovirus) to be replicated and packaged by a host cell. A number of such helper viruses have been identified, including adenoviruses, herpes viruses and poxviruses such as vaccinia. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Ban viruses (EBV), cytomegaloviruses (CMV) and pseudorabies viruses (PRV).

"Percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, those described in Current Protocols in Molecular Biology (Ausubel et al., eds., 1987), Supp. 30, section 7.7.18, Table 7.7.1, and including BLAST, BLAST-2, ALIGN or Megalign (DNASTAR) software. A preferred alignment program is ALIGN Plus (Scientific and Educational Software, Pennsylvania). Those skilled in the art can determine appropriate parameters for measuring alignment, including any algorithms needed to achieve maximal alignment over the full length of the sequences being compared. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

An "isolated" molecule (e.g., nucleic acid or protein) or cell means it has been identified and separated and/or recovered from a component of its natural environment.

An "effective amount" is an amount sufficient to effect beneficial or desired results, including clinical results (e.g., amelioration of symptoms, achievement of clinical endpoints, and the like). An effective amount can be administered in one or more administrations. In terms of a disease state, an effective amount is an amount sufficient to ameliorate, stabilize, or delay development of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (e.g., not worsening) state of disease, preventing spread (e.g., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

Reference to "about" a value or parameter herein includes (and describes) embodiments that are directed to that value or parameter per se. For example, description referring to "about X" includes description of "X."

As used herein, the singular form of the articles "a," "an," and "the" includes plural references unless indicated otherwise. For example, the phrase "a rAAV particle" includes one or more rAAV particles.

It is understood that aspects and embodiments of the invention described herein include "comprising," "consisting," and/or "consisting essentially of" aspects and embodiments.

III. Methods to Treat Spinal Muscular Atrophy

In some aspects, the invention provides methods and compositions for treating spinal muscular atrophy (SMA) in a primate comprising administering to the spinal cord and/or cisterna magna of the primate an effective amount of rAAV viral particles comprising a vector encoding a primate SMN. The methods can be used for treating a human with SMA, e.g., a pediatric subject, to improve the pathologies associated with spinal muscular atrophy. In some embodiments, the viral particle comprises an AAV serotype 9 capsid (AAV9 capsid) and AAV2 inverted terminal repeats. In some embodiments, the viral particle comprises a recombinant self-complementing vector genome for efficient expression of the transgene in motor neurons upon viral transduction. In some embodiments, at least $1 \times 10^{12}$ genome copies are administered to the primate.

In some aspects, the invention provides methods and compositions for ameliorating a symptom of SMA, comprising administration to the spinal cord and/or cisterna magna of a primate an effective amount of rAAV viral particles comprising a vector encoding a primate SMN. In some embodiments the symptoms of SMA include, but is not limited to, muscle wasting, paralysis, bulbar and respiratory dysfunction, motor neuron cell loss and neuromuscular junction pathology. For example, the methods can be used for ameliorating one or more symptoms in a human with SMA, e.g., a pediatric subject with SMA. Amelioration of the symptoms of SMA can be measured by improved motor muscle action potential, achieved milestones, decreased dependency on ventilation, increased quality of life and longevity. For example, improvement can be measured by less dependence on ventilation and cough assistance machines, or the use of feeding tubes. Improvement can also be measured by gross motor functions such as sitting unaided, head control and the ability to walk. Increases in motor unit number estimation (MUNE), improvement in compound motor action potential (CMAP), increase in Hammersmith functional motor score (HFMS), improvement in pulmonary functional tests (FVC), and improvement of gross muscle physiology using MRI imaging, alone or in combination are indicative of therapeutic efficacy. Milestones can be measured with respect to the subject before the treatment of the invention, in comparison with non-treated peers, or in comparison with historical records.

In some aspects of the invention, the methods and compositions are used for the treatment of humans with SMA. SMA may be caused by mutations in the SMN1 gene that encodes the SMN protein. In some embodiments of the invention, the methods are used to treat humans with a mutation in the SMN1 gene and/or in the SMN protein. In some embodiments, the expression of functional SMN in motor neurons is deficient compared to the expression of SMN in motor neurons of a human without SMA. In some embodiments, the expression of SMN is deficient in motor neurons of the brain and/or spinal cord.

There are three types of SMA in terms of disease severity which are related to the expression of SMN2 in the subject. Type I SMA is characterized by early onset (<6 months of age, with death typically <3 years of age) and a SMN2 copy number of 1-2. Type I SMA subjects never achieve the ability to sit and have respiratory and bulbar dysfunction. Type II SMA onset is typically between 6 and 18 months of age, with death typically at <30-40 years of age. Type II SMA is typically associated with a SMN2 copy number of 2-3. Type II subjects never achieve the ability to walk and eventually succumb to respiratory dysfunction. Type III SMA onset is typically at >18 months of age with death at >60 years of age. Type III SMA is associated with a SMN2 copy number of 3-4. Type III patients are often confined to a wheelchair by teenage and have no respiratory dysfunction.

In some embodiments, the invention provides methods for treating a human with Type I SMA. In some embodiments, the invention provides methods for treating a human with Type II SMA. In some embodiments, the invention provides methods for treating a human with Type III SMA. In some embodiments, the invention provides methods for treating a human with Type I or Type II SMA. In some embodiments, the invention provides methods for treating a human with Type II or Type III SMA. In some embodiments the invention provides methods for treating a human wherein the human has an smn2 copy number of 1-2, 2-3 or 3-4.

SMN2 mRNA may be identified by a NCBI RefSeq number selected from the group consisting of NM_017411.3, NM_022875.2, NM_022876.2, and NM_022877.2.

In some embodiments, the invention provides methods for treating a pediatric human subject with SMA. In some embodiments, the pediatric human subject is less than any one of 2 months of age, 3 months of age, 4 months of age, 5 months of age, 6 months of age, 7 months of age, 8 months of age, 9 months of age, 10 months of age, 11 months of age, 12 months of age, 13 months of age, 14 months of age, 15 months of age, 16 months of age, 17 months of age, 18 months of age, 1 year of age, 2 years of age, 3 years of age, 4 years of age, 5 years of age, 6 years of age, 7 years of age, 8 years of age, 9 years of age, 10 years of age, 11 years of age, 12 years of age, 13 years of age, 14 years of age, 15 years of age, 16 years of age, 17 years of age, 18 years of age. In some embodiments, the human subject is greater than 18 years of age.

In some aspects, the invention provides methods to deliver a heterologous transgene encoding a primate SMN to a motor neuron in a primate, the method comprising administering to the spinal cord or cisterna magna of the primate, an effective amount of rAAV viral particles comprising vector encoding the primate SMN1 transgene. The administration delivers the transgene product to the motor neuron's cellular environment, where the SMN mediates a beneficial effect on the cell and surrounding cells. In some embodiments the motor neurons are in the spinal cord of the primate. In some embodiments, the invention provides methods to deliver a transgene expressing human SMN to motor neurons are in the spinal cord of a human.

In some embodiments, the administration to the spinal cord and/or cisterna magna of an effective amount of rAAV viral particles comprising a vector encoding a primate SMN transduces motor neurons at the vertebrate section site of administration. In some embodiments, more than about any of 5%, 10%, 15%, 20%, 25%, 30%, 35%, 40%, 45%, 50%, 55%, 60%, 65%, 70%, 75% or 100% of motor neurons are transduced. In some embodiments, more than about any of 5%, 10%, 15%, 20%, 25%, 30%, 35%, 40%, 45%, 50%, 55%, 60%, 65%, 70%, 75% or 100% of motor neurons throughout the spinal cord are transduced (e.g., throughout the lumbar, thoracic, and cervical regions). Methods to identify motor neurons transduced by AAV expressing SMN are known in the art; for example, immunohistochemistry can be used to detect expression of SMN using an anti-SMN antibody and motor neurons can be identified using an anti-choline acetyl transferase (ChAT) antibody. In some embodiments, more than about any of 5%, 10%, 15%, 20%, 25%, 30%, 35%, 40%, 45%, 50%, 55%, 60%, 65%, 70%, 75% or 100% of motor neurons are transduced in an animal model of SMA, e.g., a mouse model of SMA, or in a nonhuman primate.

In some embodiments, the transduction of motor neurons following administration to the spinal cord and/or cisterna magna of a primate an effective amount of AAV viral particles comprising a vector encoding a primate SMN results in the expression of SMN to provide benefit to a primate with SMA. For example, reconstituting SMN levels to 20-30% wild type levels in the spinal cord is sufficient to provide some level of therapeutic benefit in a mouse model of SMA. In some embodiments of the invention, administration to the spinal cord and/or cisterna magna of an AAV viral particle comprising a transgene encoding a primate SMN results in expression of at least about any of 20%, 25%, 30%, 35%, 40%, 45%, 50%, 55%, 60%, 65%, 70%, 75%, 80%, 85%, 90%, 95% or 100% of levels of SMN expression in a normal individual. Methods to measure expression of SMN are known in the art; for example, using an anti-SMN antibody. For example, the expression of SMN can be measured in a mouse model of SMA.

In some embodiments of the invention, the methods comprise administration to the spinal cord and/or cisterna magna of a primate an effective amount of AAV viral particles comprising a vector encoding a primate SMN for treating a primate, e.g., a human, with SMA. In some embodiments, the composition is injected to one or more intrathecal spaces in the spinal cord and or in the cisterna magna to allow expression of SMN in motor neurons. In some embodiments, the composition is injected into the cisterna magna. In some embodiments, the composition is injected into the subarachnoid space of the spinal column at one or more locations in the cervical, thoracic, lumbar or sacral regions of the spinal cord. In some embodiments, the composition is injected into any one of one, two, three, four, five, six, seven, eight, nine, ten or more than ten locations in the subarachnoid space of the spinal cord. In some embodiments, the composition is injected to the cisterna magna and the spinal cord. In some embodiments, the composition is injected to the cisterna magna and into any one of one, two, three, four, five, six, seven, eight, nine, ten or more than ten locations in the subarachnoid space of the spinal cord. In some embodiments, the composition is injected into the subarachnoid space of the spinal cord using a catheter or other devices for intrathecal injection known in the art.

In some embodiments the rAAV viral particles are administered to more than one location simultaneously or sequentially. In some embodiment, multiple injections of rAAV viral particles are no more than one hour, two hours, three hours, four hours, five hours, six hours, nine hours, twelve hours or 24 hours apart.

The human brain structure can be correlated to similar structures in the brain of another mammal. Most mammals, including humans and rodents, show a similar topographical organization of the entorhinal hippocampus projections, with neurons in the lateral part of both the lateral and medial entorhinal cortex projecting to the dorsal part or septal pole of the hippocampus, whereas the projection to the ventral hippocampus originates primarily from neurons in medial parts of the entorhinal cortex (Principles of Neural Science, 4th ed., eds Kandel et al., McGraw Hill, 1991; The Rat Nervous System, 2nd ed., ed. Paxinos, Academic Press, 1995). Furthermore, layer II cells of the entorhinal cortex project to the dentate gyrus, and they terminate in the outer two thirds of the molecular layer of the dentate gyrus. The axons from layer III cells project bilaterally to the cornu ammonis areas CA1 and CA3 of the hippocampus, terminating in the stratum lacunose molecular layer. Moreover, one of ordinary skill in the art would readily know how to identify structures in the human brain, see, e.g., The Human Brain: Surface, Three Dimensional Sectional Anatomy With MRI, and Blood Supply, 2nd ed., eds. Deuteron et al., Springer Vela, 1999; Atlas of the Human Brain, eds. Mai et al., Academic Press; 1997; and Co Planar Sterotaxic Atlas of the Human Brain: 3 Dimensional Proportional System: An Approach to Cerebral Imaging, eds. Tamarack et al., Thyme Medical Pub., 1988. For identification of structures in the mouse brain, see, e.g., The Mouse Brain in Sterotaxic Coordinates, 2nd ed., Academic Press, 2000.

In some embodiments, the methods comprise administration to the spinal cord and/or cisterna magna of a primate an effective amount of AAV viral particles comprising a vector encoding a primate SMN. In some embodiments, the viral titer of the composition is at least about any of $5 \times 10^{12}$, $6 \times 10^{12}$, $7 \times 10^{12}$, $8 \times 10^{12}$, $9 \times 10^{12}$, $10 \times 10^{12}$, $11 \times 10^{12}$, $15 \times 10^{12}$, $20 \times 10^{12}$, $25 \times 10^{12}$, $30 \times 10^{12}$, or $50 \times 10^{12}$ genome copies/mL. In some embodiments, the viral titer of the composition is about any of $5 \times 10^{12}$ to $6 \times 10^{12}$, $6 \times 10^{12}$ to $7 \times 10^{12}$, $7 \times 10^{12}$ to $8 \times 10^{12}$, $8 \times 10^{12}$ to $9 \times 10^{12}$, $9 \times 10^{12}$ to $10 \times 10^{12}$, $10 \times 10^{12}$ to $11 \times 10^{12}$, $11 \times 10^{12}$ to $15 \times 10^{12}$, $15 \times 10^{12}$ to $20 \times 10^{12}$, $20 \times 10^{12}$ to $25 \times 10^{12}$, $25 \times 10^{12}$ to $30 \times 10^{12}$, $30 \times 10^{12}$ to $50 \times 10^{12}$, or $50 \times 10^{12}$ to $100 \times 10^{12}$ genome copies/mL. In some embodiments, the viral titer of the composition is about any of $5 \times 10^{12}$ to $10 \times 10^{12}$, $10 \times 10^{12}$ to $25 \times 10^{12}$, or $25 \times 10^{12}$ to $50 \times 10^{12}$ genome copies/mL. In some embodiments, the viral titer of the composition is at least about any of $5 \times 10^{9}$, $6 \times 10^{9}$, $7 \times 10^{9}$, $8 \times 10^{9}$, $9 \times 10^{9}$, $10 \times 10^{9}$, $11 \times 10^{9}$, $15 \times 10^{9}$, $20 \times 10^{9}$, $25 \times 10^{9}$, $30 \times 10^{9}$, or $50 \times 10^{9}$ transducing units/mL. In some embodiments, the viral titer of the composition is about any of $5 \times 10^{9}$ to $6 \times 10^{9}$, $6 \times 10^{9}$ to $7 \times 10^{9}$, $7 \times 10^{9}$ to $8 \times 10^{9}$, $8 \times 10^{9}$ to $9 \times 10^{9}$, $9 \times 10^{9}$ to $10 \times 10^{9}$, $10 \times 10^{9}$ to $11 \times 10^{9}$, $11 \times 10^{9}$ to $15 \times 10^{9}$, $15 \times 10^{9}$ to $20 \times 10^{9}$, $20 \times 10^{9}$ to $25 \times 10^{9}$, $25 \times 10^{9}$ to $30 \times 10^{9}$, $30 \times 10^{9}$ to $50 \times 10^{9}$ or $50 \times 10^{9}$ to $100 \times 10^{9}$ transducing units/mL. In some embodiments, the viral titer of the composition is about any of $5 \times 10^{9}$ to $10 \times 10^{9}$, $10 \times 10^{9}$ to $15 \times 10^{9}$, $15 \times 10^{9}$ to $25 \times 10^{9}$, or $25 \times 10^{9}$ to $50 \times 10^{9}$ transducing units/mL. In some embodiments, the viral titer of the composition is at least any of about $5 \times 10^{10}$, $6 \times 10^{10}$, $7 \times 10^{10}$, $8 \times 10^{10}$, $9 \times 10^{10}$, $10 \times 10^{10}$, $11 \times 10^{10}$, $15 \times 10^{10}$, $20 \times 10^{10}$, $25 \times 10^{10}$, $30 \times 10^{10}$, $40 \times 10^{10}$, or $50 \times 10^{10}$ infectious units/mL. In some embodiments, the viral titer of the composition is at least any of about $5 \times 10^{10}$ to $6 \times 10^{10}$, $6 \times 10^{10}$ to $7 \times 10^{10}$, $7 \times 10^{10}$ to $8 \times 10^{10}$, $8 \times 10^{10}$ to $9 \times 10^{10}$, $9 \times 10^{10}$ to $10 \times 10^{10}$, $10 \times 10^{10}$ to $11 \times 10^{10}$, $11 \times 10^{10}$ to $15 \times 10^{10}$, $15 \times 10^{10}$ to $20 \times 10^{10}$, $20 \times 10^{10}$ to $25 \times 10^{10}$, $25 \times 10^{10}$ to $30 \times 10^{10}$, $30 \times 10^{10}$ to $40 \times 10^{10}$, $40 \times 10^{10}$ to $50 \times 10^{10}$, or $50 \times 10^{10}$ to $100 \times 10^{10}$ infectious units/mL. In some embodiments, the viral titer of the composition is at least any of about $5 \times 10^{10}$ to $10 \times 10^{10}$, $10 \times 10^{10}$ to $15 \times 10^{10}$, $15 \times 10^{10}$ to $25 \times 10^{10}$, or $25 \times 10^{10}$ to $50 \times 10^{10}$ infectious units/mL. In further embodiments, the administration of a high titer AAV composition is accomplished by direct injection into the spinal cord, intrathecal injection, and/or injection to the cisterna magna of primate, e.g., a human with SMA.

In some embodiments, the methods comprise administration to the spinal cord and/or cisterna magna of a primate (e.g., a human) an effective amount of AAV viral particles comprising a vector encoding a primate SMN to a primate. In some embodiments, the dose of viral particles administered to the primate is at least about any of $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7.5 \times 10^{12}$, or $1 \times 10^{13}$ genome copies/kg of body weight. In some embodiments, the dose of viral particles administered to the primate is about any of $1 \times 10^{11}$ to $2 \times 10^{11}$, $2 \times 10^{11}$ to $3 \times 10^{11}$, $3 \times 10^{11}$ to $4 \times 10^{11}$, $4 \times 10^{11}$ to $5 \times 10^{11}$, $5 \times 10^{11}$ to $6 \times 10^{11}$, $6 \times 10^{11}$ to $7 \times 10^{11}$, $7 \times 10^{11}$ to $8 \times 10^{11}$, $8 \times 10^{11}$ to $9 \times 10^{11}$, $9 \times 10^{11}$ to $1 \times 10^{12}$, $1 \times 10^{12}$ to $2 \times 10^{12}$, $2 \times 10^{12}$ to $3 \times 10^{12}$, $3 \times 10^{12}$ to $4 \times 10^{12}$, $4 \times 10^{12}$ to $5 \times 10^{12}$, or $5 \times 10^{12}$ to $10 \times 10^{12}$ genome copies/kg of body weight. In some embodiments, the dose of viral particles administered to the primate is about any of $1 \times 10^{11}$ to $5 \times 10^{11}$, $5 \times 10^{11}$ to $1 \times 10^{12}$, or $1 \times 10^{12}$ to $5 \times 10^{12}$ genome copies/kg of body weight.

In some embodiments, the methods comprise administration to the spinal cord and/or cisterna magna of a primate (e.g., a human) an effective amount of AAV viral particles comprising a vector encoding a primate SMN to a primate. In some embodiments, the total amount of viral particles administered to the primate is at least about any of $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, $9 \times 10^{13}$, $1 \times 10^{14}$ genome copies. In some embodiments, the total amount of viral particles administered to the primate is about any of $1 \times 10^{12}$ to $2 \times 10^{12}$, $2 \times 10^{12}$ to $3 \times 10^{12}$, $3 \times 10^{12}$ to $4 \times 10^{12}$, $4 \times 10^{12}$ to $5 \times 10^{12}$, $5 \times 10^{12}$ to $6 \times 10^{12}$, $6 \times 10^{12}$ to $7 \times 10^{12}$, $7 \times 10^{12}$ to $8 \times 10^{12}$, $8 \times 10^{12}$ to $9 \times 10^{12}$, $9 \times 10^{12}$ to $1 \times 10^{13}$, $1 \times 10^{13}$ to $2 \times 10^{13}$, $2 \times 10^{13}$ to $3 \times 10^{13}$, $3 \times 10^{13}$ to $4 \times 10^{13}$, $4 \times 10^{13}$ to $5 \times 10^{13}$, $5 \times 10^{13}$ to $6 \times 10^{13}$, $6 \times 10^{13}$ to $7 \times 10^{13}$, $7 \times 10^{13}$ to $8 \times 10^{13}$, $8 \times 10^{13}$ to $9 \times 10^{13}$, $9 \times 10^{13}$ to $1 \times 10^{14}$ genome copies. In some embodiments, the total amount of viral particles administered to the primate is about any of $1 \times 10^{12}$ to $5 \times 10^{12}$, $5 \times 10^{12}$ to $1 \times 10^{13}$, $1 \times 10^{13}$ to $5 \times 10^{13}$, or $5 \times 10^{13}$ to $1 \times 10^{14}$ genome copies.

In some embodiments of the invention, the volume of the composition injected to the cisterna magna or subarachnoid space of the spinal column is more than about any one of 1 μl, 10 μl, 100 μl, 1 mL, 2 mL, 3 mL, 4 mL, 5 mL, 6 mL, 7 mL, 8 mL, 9 mL, 10 mL, 25 mL or 50 mL, or any amount therebetween.

In some embodiments of the invention, the total amount of viral particles are administered to more than one location. For example, a total dose of $3 \times 10^{13}$ genome copies can be administered by injecting $1 \times 10^{13}$ genome copies to the cisterna magna, $1 \times 10^{13}$ genome copies to a thoracic subarachnoid space, and $1 \times 10^{13}$ genome copies to a lumbar subarachnoid space. In some embodiments, the viral particles are evenly distributed between injection locations. In some embodiments, the viral particles are not evenly distributed between injection sites; e.g., $2 \times 10^{13}$ genome copies to the cisterna magna and $1 \times 10^{13}$ genome copies to a lumbar subarachnoid space.

Compositions of the invention (e.g., AAV viral particles comprising a transgene encoding a primate SMN) can be used either alone or in combination with one or more additional therapeutic agents for treating SMA. The interval between sequential administration can be in terms of at least (or, alternatively, less than) minutes, hours, or days.

IV. Expression Constructs

Survival Motor Neuron (SMN) Nucleic Acid and Protein

Two SMN genes are present on chromosome 5q13, the SMN1 gene and the SMN2 gene. The coding sequence of SMN2 differs from the SMN1 sequence by five nucleotides. Although there is a difference in the nucleic acid sequence, the amino acid sequence remains unaltered. However, a single nucleotide difference from cystine (C) to thymine (T) in exon 7 of SMN2 results in alternative splicing of SMN2 transcripts. The SMN2 gene is found exclusively in humans, while the SMN1 gene is found in human as well as non-human primates such as the chimpanzee. See Rochette et al., Human Genetics, 2001, 108(3):255-266. The SMN1 gene encodes for the SMN protein which is particularly abundant in motor neurons of the spinal cord but found at reduced levels in subjects with spinal muscular atrophy (SMA), an autosomal recessive disorder that results from homozygous mutations or deletions in the SMN1 gene. See Coovert et al, Hum Mol Genet, 1997, 6(8):1205-14 and Fallini et al, Brain Res., 2012, 1462:81-92 for a review on the role of SMN in SMA, which are hereby incorporated by reference in their entirety.

The present invention provides an isolated nucleic acid (e.g., a transgene) that encodes an SMN protein, wherein the isolated nucleic acid can be packaged in any AAV viral particle described herein. Accordingly, in one aspect, the invention provides for an isolated nucleic acid encoding an SMN protein from a primate such as a human. In some embodiments, the isolated nucleic acid encodes an SMN protein from a primate taxonomy selected from the group consisting of a family Tarsiidae, family Callitrichidae, family Cebidae, family Aotidae, family Pitheciidae, family Atelidae, family Cercopithecidae, family Hylobatidae, and family Hominidae. In some embodiments, the isolated nucleic acid encodes an SMN protein from a primate selected from the group consisting of a *Homo sapien*, a *Macaca mulatta*, a *Pan troglodytes*, a *Papio anubis*, a *Nomascus leucogenys*, a *Pongo abelii*, a *Gorilla gorilla*, a *Saimiri boliviensis*, and a *Pan paniscus*. In some embodiments, the isolated nucleic acid encodes an SMN1 mRNA identified by a NCBI Reference Sequence (RefSeq) number selected from the group consisting of NM_000344.3, NM_022874.2, NM_001260664.1, and NM_001131470.2. In some embodiments, the isolated nucleic acid encodes an SMN protein identified by a NCBI RefSeq number selected from the group consisting of NP_000335.1, NP_075012.1, NP_001247593.1, XP_001156488.1, XP_001156435.1, XP_001156259.1, XP_001156201.1, XP_003266089.1, XP_003266087.1, XP_003266086.1, XP_003266090.1, NP_001124942.1, XP_004058779.1, XP_003925817.1, XP_003925818.1, XP_003925819.1, XP_003806815.1, XP_003806816.1, XP_003806817.1, and XP_003806818.1. In some embodiments, the isolated nucleic acid (e.g., the transgene) encodes an SMN protein comprising the amino acid sequence of SEQ ID NO:1. In some embodiments, the isolated nucleic acid (e.g., the transgene) comprises the nucleic acid sequence selected from the group consisting of SEQ ID NOs:2-4.

Amino acid sequence variants of any SMN protein provided herein are also contemplated. In some embodiments, the amino acid variant of an SMN protein is a naturally occurring variant of SMN. In some embodiments, the biological properties of the SMN protein can be improved by altering the amino acid sequence encoding the protein. Amino acids sequence variants of an SMN protein can be prepared by introducing appropriate modifications into the nucleic acid sequence encoding the protein or by introducing the modification by peptide synthesis. Such modifications include, for example, deletions from, insertions into, and/or substitutions within the amino acid sequence of the SMN protein. Also contemplated herein are amino acid sequence variants of any SMN protein that arise from natural mutations (e.g., natural selection) in the nucleic acid encoding the protein. Accordingly, provided herein are isolated nucleic acids encoding variants of an SMN protein, wherein the isolated nucleic acid can be packaged (e.g., as a transgene) in any AAV viral particle described herein. In some embodiments, the isolated nucleic acid encodes an SMN protein variant comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of any SMN protein described herein (e.g., human SMN protein). In some embodiments, the isolated nucleic acid encodes an SMN protein variant comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an amino acid sequence of SEQ ID NO:1. In some embodiments, the isolated nucleic acid encoding SMN comprises mutations conferring one, two, three, four, five, six, seven, eight, nine or ten amino acid substitutions while maintaining its biological function in motor neurons. In some embodiments, the resulting SMN protein can express wild-type levels of activity. In some embodiments, the resulting SMN protein is expressed at wild-type levels.

Isolated nucleic acid molecules encoding an SMN protein (e.g., an SMN protein) can be obtained by cloning or produced synthetically, or any combinations thereof. The nucleic acid can be triple-stranded, double-stranded or single-stranded, or any combination thereof. Any portion of at least one strand of the DNA can be the coding strand, also known as the sense strand, or it can be the non-coding strand, also referred to as the anti-sense strand. The isolated nucleic acids can be obtained from biological sources using any number of cloning methodologies known to those of skill in the art. The isolated nucleic acids can also be prepared by direct chemical synthesis by known methods. Nucleic acids encoding an SMN protein can be prepared by a variety of methods known in the art including, but not limited to, isolation from a natural source or preparation by oligonucleotide-mediated mutagenesis, site-directed mutagenesis, PCR mutagenesis, and cassette mutagenesis of an earlier prepared variant or a non-variant version of the SMN protein. See *Molecular Cloning: A Laboratory Manual* (Sambrook et al., 4$^{th}$ ed., Cold Spring Harbor Laboratory Press, Cold Spring Harbor, N.Y., 2012) and *Current Protocols in Molecular Biology* (F. M. Ausubel, et al. eds., 2003).

In some embodiments, the transgene (e.g., the SMN1 transgene) is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit β-globin promoter (CAG promoter; Niwa et al., *Gene*, 1991, 108(2):193-9) and the elongation factor 1-alpha promoter (EF1-alpha) promoter (Kim et al., *Gene*, 1990, 91(2):217-23 and Guo et al., *Gene Ther.*, 1996, 3(9):802-10). In some embodiments, the promoter comprises a human β-glucuronidase promoter or a cytomegalovirus enhancer linked to a chicken β-actin promoter. The promoter can be a constitutive, inducible or repressible promoter. In some embodiments, the transgene encodes any SMN protein described herein (e.g., primate SMN) and is operable linked to a promoter. In some embodiments, the transgene encodes a human SMN protein and is operable linked to a promoter. In some embodiments, the transgene encodes a human SMN protein comprising the amino acid sequence of SEQ ID NO:1 and is operable linked to a promoter. In some embodiments, the transgene comprises a nucleic acid sequence selected from the group consisting of SEQ ID NOs:2-4 and is operable linked to a promoter.

Recombinant Viral Vector

The present invention contemplates the use of a recombinant viral genome for introduction of one or more nucleic acid sequences encoding for an SMN protein described herein for packaging into an AAV viral particle. The recombinant viral genome may include any element to establish the expression of an SMN protein, for example, a promoter, an SMN1 transgene, an ITR, a ribosome binding element, terminator, enhancer, selection marker, intron, polyA signal, and/or origin of replication. In some embodiments, the recombinant viral genome is derived from the nucleic acid of SEQ ID NO:5. In some embodiments, the recombinant viral genome is derived from the nucleic acid of SEQ ID NO:6.

V. Viral Particles and Methods of Producing Viral Particles rAAV Viral Particles In some embodiments, the viral particle is a recombinant AAV particle comprising a nucleic acid comprising a sequence encoding an SMN protein (e.g., human SMN protein) described herein flanked by one or two ITRs. The nucleic acid is encapsidated in the AAV particle. The AAV particle also comprises capsid proteins. In some embodiments, the nucleic acid comprises the protein coding sequence(s) of interest (e.g., a transgene encoding an SMN protein) operatively linked components in the direction of transcription, control sequences including transcription initiation and termination sequences, thereby forming an expression cassette. The expression cassette is flanked on the 5' and 3' end by at least one functional AAV ITR sequences. By "functional AAV ITR sequences" it is meant that the ITR sequences function as intended for the rescue, replication and packaging of the AAV virion. See Davidson et al., *PNAS*, 2000, 97(7)3428-32; Passini et al., *J. Virol.*, 2003, 77(12):7034-40; and Pechan et al., *Gene Ther.*, 2009, 16:10-16, all of which are incorporated herein in their entirety by reference. For practicing some aspects of the invention, the recombinant vectors comprise at least all of the sequences of AAV essential for encapsidation and the physical structures for infection by the rAAV. AAV ITRs for use in the vectors of the invention need not have a wild-type nucleotide sequence (e.g., as described in Kotin, *Hum. Gene Ther.*, 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., *PNAS*, 2002, 99(18): 11854-6; Gao et al., *PNAS*, 2003, 100(10):6081-6; and Bossis et al., *J. Virol.*, 2003, 77(12):6799-810. Use of any AAV serotype is considered within the scope of the present invention. In some embodiments, a rAAV vector is a vector derived from an AAV serotype, including without limitation, AAV1, AAV2, AAV3, AAV4, AAV5, AA6, AAV7, AAV8, AAV9, AAVrh.8, AAVrh.10, AAV11, or AAV12 or the like. In some embodiments, the nucleic acid in the AAV comprises an ITR of AAV1, AAV2, AAV3, AAV4, AAV5, AA6, AAV7, AAV8, AAV9, AAVrh.8, AAVrh.10, AAV11, AAV12 or the like. In some embodiments, the nucleic acid in the AAV further encodes any one or more SMN protein (e.g., human SMN protein) as described herein. For example, the nucleic acid in the AAV can comprise at least one ITR of any AAV serotype contemplated herein and can further encode an SMN protein comprising the amino acid of SEQ ID NO:1. In some embodiments, the nucleic acid in the AAV can comprise at least one ITR of any AAV serotype contemplated herein and the nucleic acid sequence selected from the group consisting of SEQ ID NOs:2-4. In some embodiments, the nucleic acid in the AAV comprises the nucleic acid sequence selected from the group consisting of SEQ ID NOs:2-4, and is flanked by at least one AAV ITR. In some embodiments, a nucleic acid encoding an SMN protein comprising the amino acid sequence of SEQ ID NO:1, and is flanked by at least ITR. In some embodiments, the nucleic acid in the AAV comprises the nucleic acid sequence selected from the group consisting of SEQ ID NOs:5 and 6. In further embodiments, the rAAV particle comprises capsid proteins of AAV1, AAV2, AAV3, AAV4, AAV5, AA6, AAV7, AAV8, AAV9, AAVrh.8, AAVrh.10, AAV11, AAV12 or the like. In further embodiments, the rAAV particle comprises capsid proteins of an AAV serotype from Clades A-F (Gao, et al. *J. Virol.* 2004, 78(12):6381). In some embodiments, the nucleic acid in the AAV comprises the nucleic acid sequence selected from the group consisting of SEQ ID NOs:2-4, and is flanked by at least one AAV2 ITR.

Different AAV serotypes are used to optimize transduction of particular target cells or to target specific cell types within a particular target tissue (e.g., a diseased tissue). A rAAV particle can comprise viral proteins and viral nucleic acids of the same serotype or a mixed serotype. For example, a rAAV particle can comprise AAV9 capsid proteins and at least one AAV2 ITR or it can comprise AAV2 capsid proteins and at least one AAV9 ITR. In yet another example, a rAAV particle can comprise capsid proteins from both AAV9 and AAV2, and further comprise at least one AAV2 ITR. Any combination of AAV serotypes for production of a rAAV particle is provided herein as if each combination had been expressly stated herein. In some embodiments, the invention provides rAAV particles comprising AAV9 capsid proteins and a nucleic acid encoding a primate SMN, e.g., a human SMN, flanked by at least one AAV2 ITR.

Self-Complementary AAV Viral Genomes

In some aspects, the invention provides viral particles comprising a recombinant self-complementing genome. AAV viral particles with self-complementing genomes and methods of use of self-complementing AAV genomes are described in U.S. Pat. Nos. 6,596,535; 7,125,717; 7,765,583; 7,785,888; 7,790,154; 7,846,729; 8,093,054; and 8,361,457; and Wang Z., et al., (2003) Gene Ther 10:2105-2111, each of which are incorporated herein by reference in its entirety. An rAAV comprising a self-complementing genome, will quickly form a double stranded DNA molecule by virtue of its partially complementing sequences (e.g., complementing coding and non-coding strands of a transgene). In some embodiments, the invention provides an AAV viral particle comprising an AAV genome, wherein the rAAV genome comprises a first heterologous polynucleotide sequence (e.g., an SMN1 coding strand) and a second heterologous polynucleotide sequence (e.g., an SMN1 non-coding or antisense strand) wherein the first heterologous polynucleotide sequence can form intrastrand base pairs with the second polynucleotide sequence along most or all of its length. In some embodiments, the first heterologous polynucleotide sequence and a second heterologous polynucleotide sequence are linked by a sequence that facilitates intrastrand basepairing; e.g., a hairpin DNA structure. Hairpin structures are known in the art, for example in siRNA molecules. In some embodiments, the first heterologous polynucleotide sequence and a second heterologous polynucleotide sequence are linked by a mutated ITR (e.g., the right ITR). In some embodiments, the ITR comprises the polynucleotide sequence 5'-CACTCCCTCTCT-GCGCGCTCGCTCGCTCACT GAGGCCGGGCGAC-CAAAGGTCGCCCACGCCCGGGCTTTGCCCGGGCG-3' (SEQ ID NO:7). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR. In some embodiments, the invention provides AAV viral particles comprising a recombinant viral genome comprising a functional AAV2 ITR, a first polynucleotide sequence encoding a primate SMN, a mutated AAV2 ITR comprising a deletion of the D region and lacking a functional terminal resolution sequence, a second polynucleotide sequence comprising the complementary sequence to the sequence encoding the primate SMN of the first polynucleotide sequence and a functional AAV2 ITR. The recombinant viral genome of the viral particles of the invention can be derived from AAV vector plasmids comprising the polynucleotide sequences of SEQ ID NOs:5 or 6.

Production of AAV Particles

The rAAV particles can be produced using methods know in the art. See, e.g., U.S. Pat. Nos. 6,566,118; 6,989,264; and 6,995,006. In practicing the invention, host cells for producing rAAV particles include mammalian cells, insect cells, plant cells, microorganisms and yeast. Host cells can also be packaging cells in which the AAV rep and cap genes are stably maintained in the host cell or producer cells in which the AAV vector genome is stably maintained. Exemplary packaging and producer cells are derived from 293, A549 or HeLa cells. AAV vectors are purified and formulated using standard techniques known in the art.

In some aspects, a method is provided for producing any rAAV particle as disclosed herein comprising (a) culturing a host cell under a condition that rAAV particles are produced, wherein the host cell comprises (i) one or more AAV package genes, wherein each said AAV packaging gene encodes an AAV replication and/or encapsidation protein; (ii) an rAAV pro-vector comprising a nucleic acid encoding any SMN protein disclosed herein flanked by at least one AAV ITR, and (iii) an AAV helper function; and (b) recovering the rAAV particles produced by the host cell. In some embodiments, a nucleic acid encodes an SMN protein of SEQ ID NO:1. In some embodiments, said at least one AAV ITR is selected from the group consisting of AAV1, AAV2, AAV3, AAV4, AAV5, AA6, AAV7, AAV8, AAV9, AAV8rh, AAV10hr, AAV11, AAV12 ITR or the like. In some embodiments, said encapsidation protein is selected from the group consisting of AAV1, AAV2, AAV3, AAV4, AAV5, AA6, AAV7, AAV8, AAV9, AAV8rh, AAVrh10, AAV10, AAV11, AAV12 capsid protein and the like. In further embodiments, the rAAV particle comprises capsid proteins of an AAV serotype from Clades A-F. In some embodiments, the rAAV particles comprise an AAV9 capsid and a recombinant self-complementing genome comprising AAV2 ITRs, a mutant AAV2 ITR and a transgene encoding a primate SMN. In a further embodiment, the rAAV particles are purified. The term "purified" as used herein includes a preparation of rAAV particles devoid of at least some of the other components that may also be present where the rAAV particles naturally occur or are initially prepared from. Thus, for example, isolated rAAV particles may be prepared using a purification technique to enrich it from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

Also provided herein are pharmaceutical compositions comprising a rAAV particle comprising a transgene encoding an SMN protein of the invention and a pharmaceutically acceptable carrier. The pharmaceutical compositions may be suitable for any mode of administration described herein. A pharmaceutical composition of a rAAV comprising a nucleic acid encoding an SMN protein described herein can be introduced systemically, e.g., by intravenous injection, by catheter, see U.S. Pat. No. 5,328,470, or by stereotactic injection, Chen et al., 1994, PNAS, 91: 3054-3057.

In some embodiments, the pharmaceutical compositions comprising a rAAV described herein and a pharmaceutically acceptable carrier is suitable for administration to human. Such carriers are well known in the art (see, e.g., Remington's Pharmaceutical Sciences, 15th Edition, pp. 1035-1038 and 1570-1580). In some embodiments, the pharmaceutical compositions comprising a rAAV described herein and a pharmaceutically acceptable carrier is suitable for intrathecal injection. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution.

VI. Articles of Manufacture and Kits

Also provided are kits or articles of manufacture for use in the methods described herein. In aspects, the kits comprise the compositions described herein (e.g., rAAV particles comprising a transgene encoding a primate SMN) in suitable packaging. Suitable packaging for compositions (such as intrathecal compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present invention also provides kits comprising compositions described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein. For example, in some embodiments, the kit comprises an rAAV comprising a transgene encoding a primate SMN for intrathecal delivery of at least 1×10$^{12}$ genome copies to a primate as described herein, a pharmaceutically acceptable carrier suitable for intrathecal injection, and one or more of: a buffer, a diluent, a filter, a needle, a syringe, and a package insert with instructions for performing intrathecal injections.

EXAMPLES

Example 1

Translational Fidelity of Intrathecal Delivery of scAAV9-SMN1 for Spinal Muscular Atrophy The potential of intrathecal delivery of a recombinant AAV vector encoding survival motor neuron 1 (SMN1) as a therapeutic approach for spinal muscular atrophy (SMA) was investigated. First, a dose-response study in SMA mice was performed to determine the minimum number of motor neurons that needed to be transduced for therapeutic benefit. Second, the feasibility of widespread gene delivery via intrathecal delivery of the recombinant viral vector to a large mammal model, specifically juvenile pigs, was ascertained. Third, applicability of widespread gene delivery via intrathecal delivery of the recombinant viral vector in non-human primates (NHP) was investigated.

Methods

Recombinant Self-Complementary AAV Vectors

Figure 6:
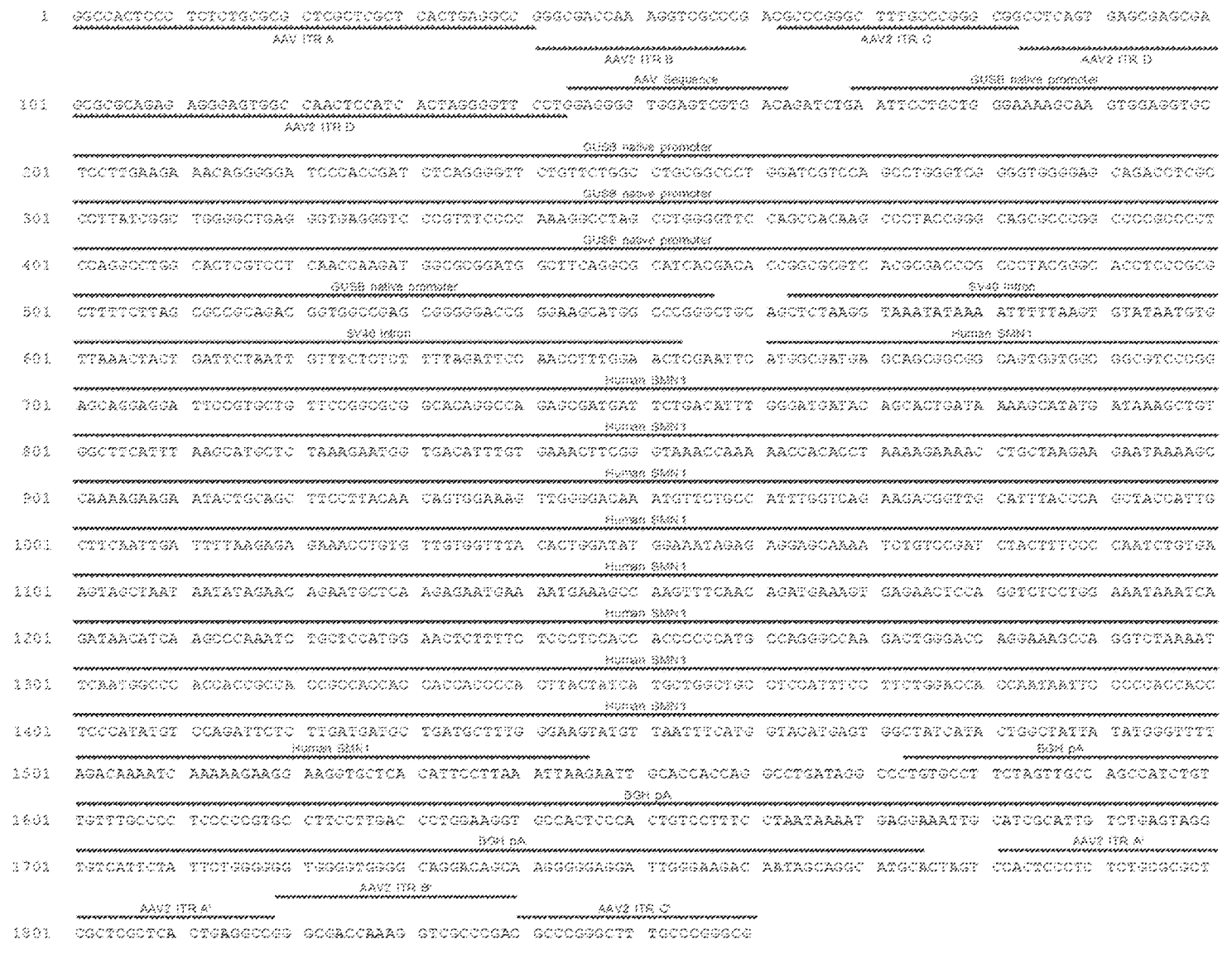
Figure 7:
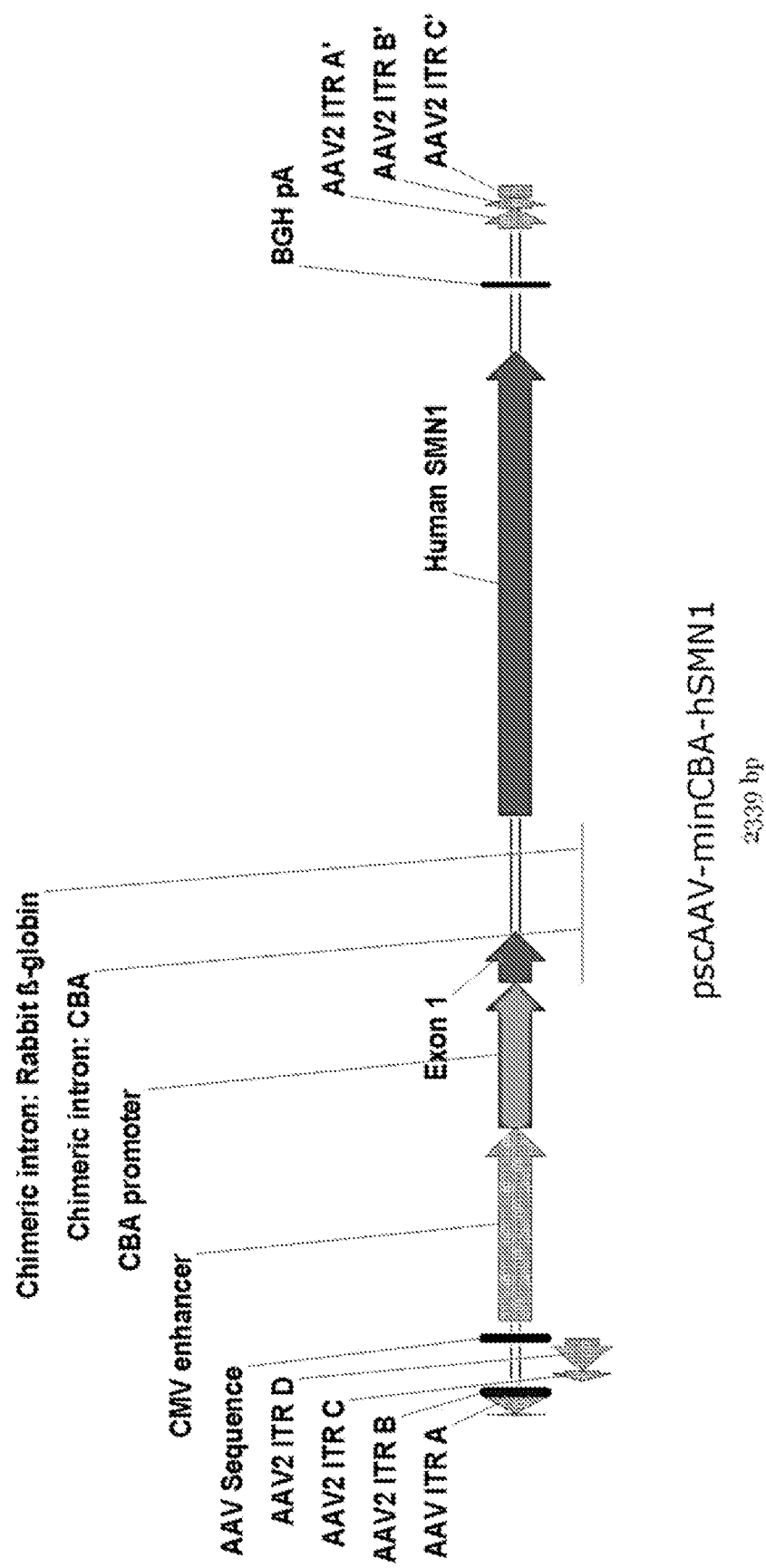
FIG. 7 shows a plasmid map of pscAAV-minCBA hSMN1.

The open reading frame of the human SMN1 was cloned into a self-complementary AAV2-ITR plasmid that contained the 0.4 kb human β-glucuronidase promoter (FIGS. 5 and 6), and packaged into serotype-9 capsid by triple-plasmid co-transfection to generate scAAV9-hSMN1. For the intrathecal delivery experiments in large animal models, the human β-glucuronidase promoter was replaced with a 0.9 kb cytomegalovirus enhancer/chicken β-actin promoter, and packaged into serotype-9 capsid by triple-plasmid co-transfection to generate scAAV9-eGFP (FIGS. 7 and 8). The titers of the scAAV9-hSMN1 and scAAV9-eGFP preparations were 8.3e12 and 4.3e12 genome copies (gc) per ml, respectively.

Mouse Surgeries

Breeding pairs of heterozygote SMA mice (SMN$^{+/-}$, hSMN2$^{+/+}$, SMNΔ7$^{+/+}$) were mated as described previously (Passini et al., 2010). On the day of birth (P$_0$), each pup received 3 injections (2 µl at each site) into the cerebral lateral ventricles of both hemispheres and into the lumbar cord for a total volume of 6 µl per mouse. Although this method of delivery targeted the CNS widely, the cervical region showed a lower level of transduction compared to the lumbar and thoracic regions because of its relative distal location to the lumbar injections (Passini et al., 2010). The scAAV9-hSMN1 vector was injected either at full strength at 5e10 gc per mouse, or diluted in saline to deliver lower final doses of 1e10 and 1e9 gc per mouse. All the injections were performed with a finely drawn glass micropipette needle as previously described (Passini et al., 2010). Following the injections, the pups were toe-clipped and genotyped to identify homozygote (SMN$^{-/-}$, hSMN2$^{+/+}$, SMNΔ7$^{+/+}$), heterozygote (SMN$^{+/-}$, hSMN2$^{+/+}$, SMNΔ7$^{+/+}$), and wild type (SMN$^{+/+}$, hSMN2$^{+/+}$, SMNΔ7$^{+/+}$) homozygous SMA mice. Following genotyping, only those determined to be SMA mice were retained as well as two wild type pups (as controls), as reported previously (Passini et al., 2011b).

Pig Surgeries

Two-month old farm pigs were obtained from Palmetto Research Swine (Reevesville, S.C.) and observed in quarantine to ensure health. The pigs were fasted the night before surgery and anesthetized with isoflourane. No paralytic was used. Pigs were positioned prone in an apparatus that has been described previously (Federici et al 2012). This apparatus allowed the pig's abdomen to hang free preventing abdominal pressure and consequently reducing venous bleeding. The lumbar region was shaved, washed and draped in the standard sterile manner. A 5 cm midline incision was performed at L5. The paraspinous muscles were dissected free from the spinous process and lamina. Next a single level lumbar laminectomy was performed using an air drill and Kerrison Ronguers. The dura mater was tented up with a single 4-0 neurolon stitch and a 4 mm incision was made at the midline. Next, an intrathecal catheter (EDM lumbar catheter, Medtronic Inc, Minneapolis Minn.) was advanced into the lumbar cistern rostrally. The catheter was advanced 50 cm into the region of the cervical spinal canal. 0.5 ml of vector was injected at the cervical site as a bolus and the catheter was then backed out 10 cm to the thoracic site. At this position, a second 0.5 ml injection was performed as a bolus. Finally, the catheter was backed out another 10 cm to the lumbar site for a third 0.5 ml injection. Prior to removal of the catheter, a purse string suture was placed with 4-0 nurolon. This was tightened immediately on removal of the catheter to prevent reflux of cerebrospinal fluid. The paraspinous muscles were re-approximated with interrupted 2-0 vicryl sutures. The fascia was closed with a running 2-0 vicryl suture. The skin was closed with interrupted inverted 3-0 vicryl sutures and a running 2-0 nylon stitch. Postoperatively, the animals were observed to ensure adequate recovery from anesthesia. Ambulation was observed over the survival period to ensure that all animals returned to their neurological baseline.

Monkey Surgeries

Six juvenile (2-3 years of age) cynomolgus monkeys that weighed ~3.5 kg were anesthetized with ketamine (Ketaset, 7 mg/kg), intubated and placed on inhaled isoflurane (1-3%). The back of the neck and lumbar spinal cord areas were shaved and cleaned with povidone-iodine and alcohol. 22-gauge spinal needles were manually guided into the intrathecal space between L4 and L5 (2 male and 1 female), and into the cisterna magna space of each animal. Correct positioning was confirmed by the flow of cerebrospinal fluid (CSF) from the needles with up to 1.5 ml of CSF collected into micro-centrifuge tubes. Syringes (3 ml) and extension lines containing scAAV9-eGFP were carefully connected to the spinal needles and 3 ml was manually injected into each site at a rate of 1 ml/min. After completing the injections, the lines were disconnected from the needles and positioning within the CSF space was confirmed by the backflow of CSF into the needle hub. Needles were then immediately removed and pressure applied to the injection site. Animals were allowed to recover from the anesthesia and observed daily with detailed cage side observations for 5 days post-surgery. One female animal that received cisterna magna and intrathecal injections had respiratory complications with a prolonged recovery from anesthesia. This animal was euthanized 24 days after treatment due to decreased appetite and weight loss. All other animals were euthanized as scheduled at 30 days post-injection. All animals were deeply anesthetized and perfused transcardially with phosphate-buffered saline and 4% paraformaldehyde. The brain, spinal cord, dorsal root ganglia, liver and spleen were harvested for immunohistochemical analysis.

Western Blot Analysis

For biochemical analysis, treated and untreated mice at 16 and 58-66 days were perfused with phosphate-buffered saline (PBS), and the spinal cords were dissected and separated into the lumbar, thoracic and cervical segments, and then snap-frozen in liquid nitrogen. Tissues were homogenized at a final concentration of 50 mg protein/ml using T-Per lysis buffer and a protease inhibitor cocktail (Pierce, Rockford, Ill.). The homogenates were cleared by centrifugation and the protein concentration was measured by BCA assay (Pierce, Rockford, Ill.). Ten to twenty micrograms of homogenate protein was resolved on a 4-12% SDS-PAGE, transferred to nitrocellulose membrane, and probed with an anti-SMN monoclonal antibody (1:5,000 BD Biosciences, San Jose, Calif.) and an anti-β-tubulin polyclonal antibody (1:750, Santa Cruz Biotechnology, Santa Cruz, Calif.). The membranes were incubated with infrared secondary antibodies (1:20,000, LI-COR Biosciences, Lincoln NB), and protein bands were visualized by quantitative fluorescence using the Odyssey software (LI-COR Biosciences).

Immunohistochemistry

For histological analysis, treated and untreated mice were first perfused with 4% paraformaldehyde (pH 7.4). The spinal cords were then removed, placed into a 30% sucrose solution for 48-72 h, embedded in Optimal Cutting Temperature (OCT) and cut into 10 µm frozen sections with a cryostat. Spinal cord sections were blocked for 1 h at room temperature (RT) and then incubated with an anti-SMN monoclonal antibody (BD Biosciences, 1:200 dilution) to locate AAV-derived hSMN, and an anti-choline acetyl transferase (ChAT) polyclonal antibody (Millipore; Burlington, Mass.; 1:100 dilution) to identify motor neurons. Primary antibodies were incubated for 1 h at RT followed by an overnight incubation at 4° C. in a humidified chamber. Spinal cord sections were then incubated for 1 h at RT with either a biotinylated anti-mouse, Cy3-conjugated anti-goat, or FITC-conjugated anti-rabbit secondary antibody (Jackson ImmunoResearch; West Grove, Pa.; 1:250 dilution). To increase the SMN and ChAT immuno-positive signals, a TSA signal amplification kit (Perkin Elmer; Waltham, Mass.) or a citric acid antigen retrieval protocol (Vector Labs; Burlingame, Calif.) were performed according to the manufacturers' instructions. Sections were cover-slipped with Vectashield mounting media (Vector Labs; Burlingame, Calif.). For GFP immunostaining in pigs and NHPs, tissue sections were incubated with a rabbit anti-eGFP antibody (Millipore; 1:500 dilution) overnight at 4° C., followed by a biotinylated anti-rabbit secondary antibody (Jackson Laboratories; 1:250 dilution) for 2 hours at room temperature, and the immuno-positive signal was visualized using a diaminobenzidine (DAB) detection assay according to the manufacturer's protocol (Vectorstain Kit, Vector Lab).

Motor Neuron Cell Counting

The number of ChAT immuno-positive cells was counted on 10 µm coronal tissue sections. Bilateral counts were performed along the rostrocaudal axis of the lumbar, thoracic and cervical segments. Cells located in laminae 8 and 9 (ventral horn) of the spinal cord that exhibited a fluorescent ChAT signal were considered motor neurons. Approximately 8-10 different levels of each spinal cord segment were counted to generate the overall average number of motor neuron counts per segment for each animal. To prevent double counting of the same cell, each section was at least 100 µm apart. Special care was also taken to compare anatomically matched sections between different animals, and cell counts were collected and recorded by a blinded observer.

Measurement of the Size of Myofibers

Skeletal muscles (quadriceps, intercostal, diaphragm) from the right side of each mouse were processed by paraffin and stained for hematoxylin-eosin to determine the myofiber cross-sectional. Approximately 500 non-overlapping myofibers from each muscle were randomly selected and photographed, and the cross-sectional area of each myofiber was then measured using Metamorph (Molecular Devices, Sunnyvale, Calif.) to generate the overall average size of the myofiber per muscle for each animal, as previously reported (Passini et al., 2010, 2011b).

Behavioral Tests

The righting reflex and grip strengths tests were performed as previously described (Passini et al., 2010, 2011b). In brief, the righting reflex test involved placing each mouse in a supine position and then measuring the time taken for the mouse to reposition itself onto all four paws. The grip strength test involved placing the forelimbs and hindlimbs on a wire grid and the mouse then gently pulled horizontally along the axis of the mesh to record the resistance.

Statistics

For the behavioral tests, and quantitation of the number of motor neurons and cross-sectional areas of myofibers, statistics were performed using a one-way ANOVA and Bonferroni multiple post hoc comparisons. The Kaplan-Meier survival curve was analyzed with the log-rank test equivalent to the Mantel-Haenszel test. All statistical analyses were performed with GraphPad Prism v4.0 (GraphPad Software, San Diego, Calif.). Values with $p<0.05$ were considered significant.

Results

Administration of Increasing Amounts of scAAV9-hSMN1 into the CNS of SMA Mice Effected Progressively Higher Motor Neuron Cell Counts and Corresponding Improvements in Muscle Physiology.

To ascertain the number of gene-modified motor neurons necessary to confer therapeutic efficacy in SMA mice, doses of 5e10, 1e10, and 1e9 genome copies (gc) of scAAV9-hSMN1 were administered into the central nervous system (CNS) of the animals. The viral vector was injected into the cerebral lateral ventricles and the lumbar spinal cord at post-natal day 0 (P0) and the animals were then sacrificed at 14 days post-injection (P14) for age-matched analysis. For each dose, the spinal cord of one cohort of mice was processed for Western blot analysis to quantitate the levels of SMN on tissue homogenates, and the spinal cord of the other cohort for immunohistochemistry to determine the spatial pattern of gene expression on tissue sections.

Figure 9:
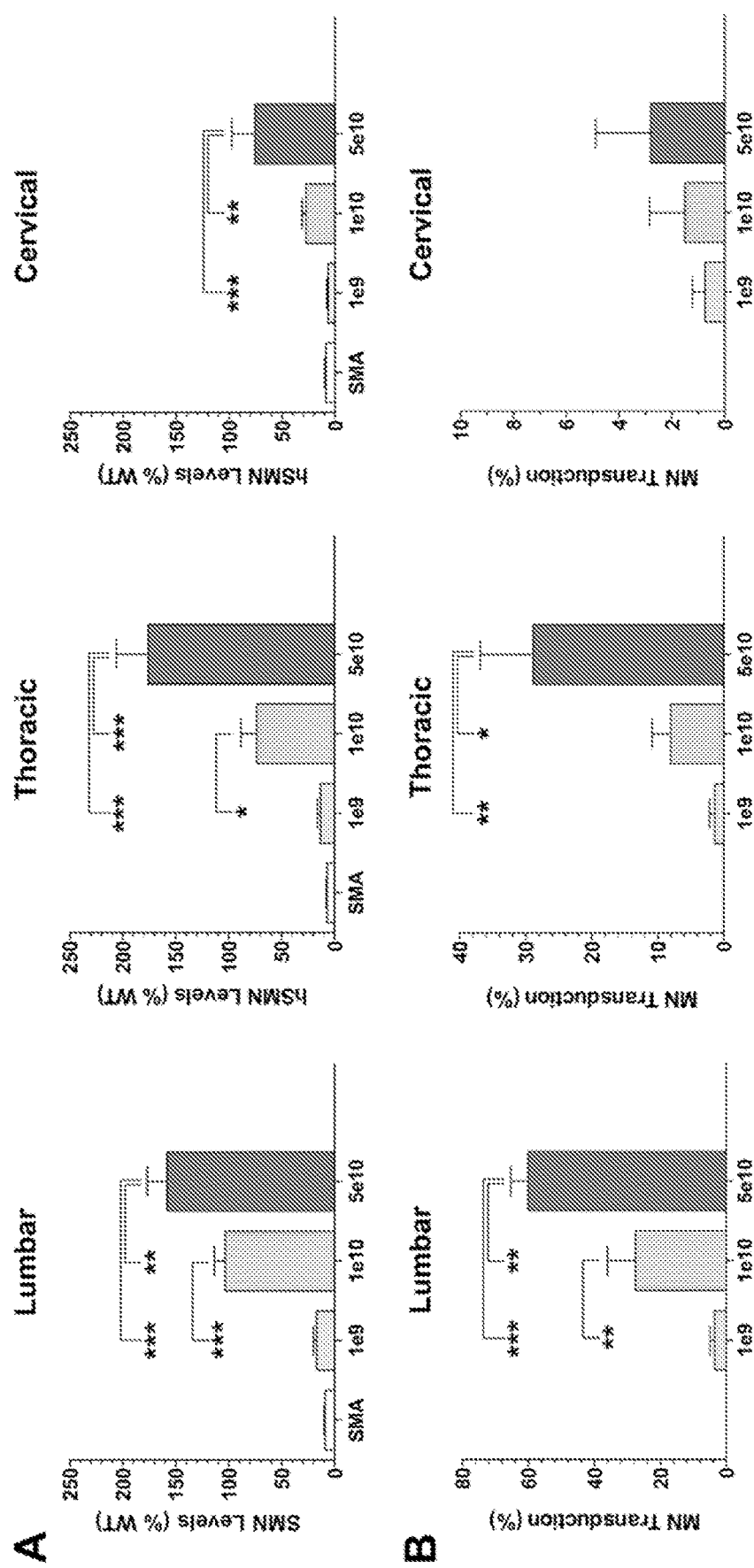
FIG. 9 shows a series of graphs that demonstrate the effect of viral dose on SMN levels and efficacy in SMA mice. A) Western blot analysis of tissue homogenates from the lumbar, thoracic, and cervical regions showed a dose response with the highest dose producing the greatest level of SMN. B) Co-localization studies of hSMN and the motor neuron marker, ChAT on frozen tissue sections allowed for a determination of the efficiency of motor neuron transduction in the lumbar and thoracic segments. However, the low levels of hSMN, regardless of dose, noted in the cervical cord precluded scoring motor neuron transduction in this region. C) The number of motor neurons (ChAT-positive) per hemisphere for all three spinal cord regions. D) The average cross-sectional areas of myofibers from the quadriceps, intercostal, and diaphragm. Statistics $*p<0.05$; $p<0.01$; $*p<0.001$.
Figure 9:
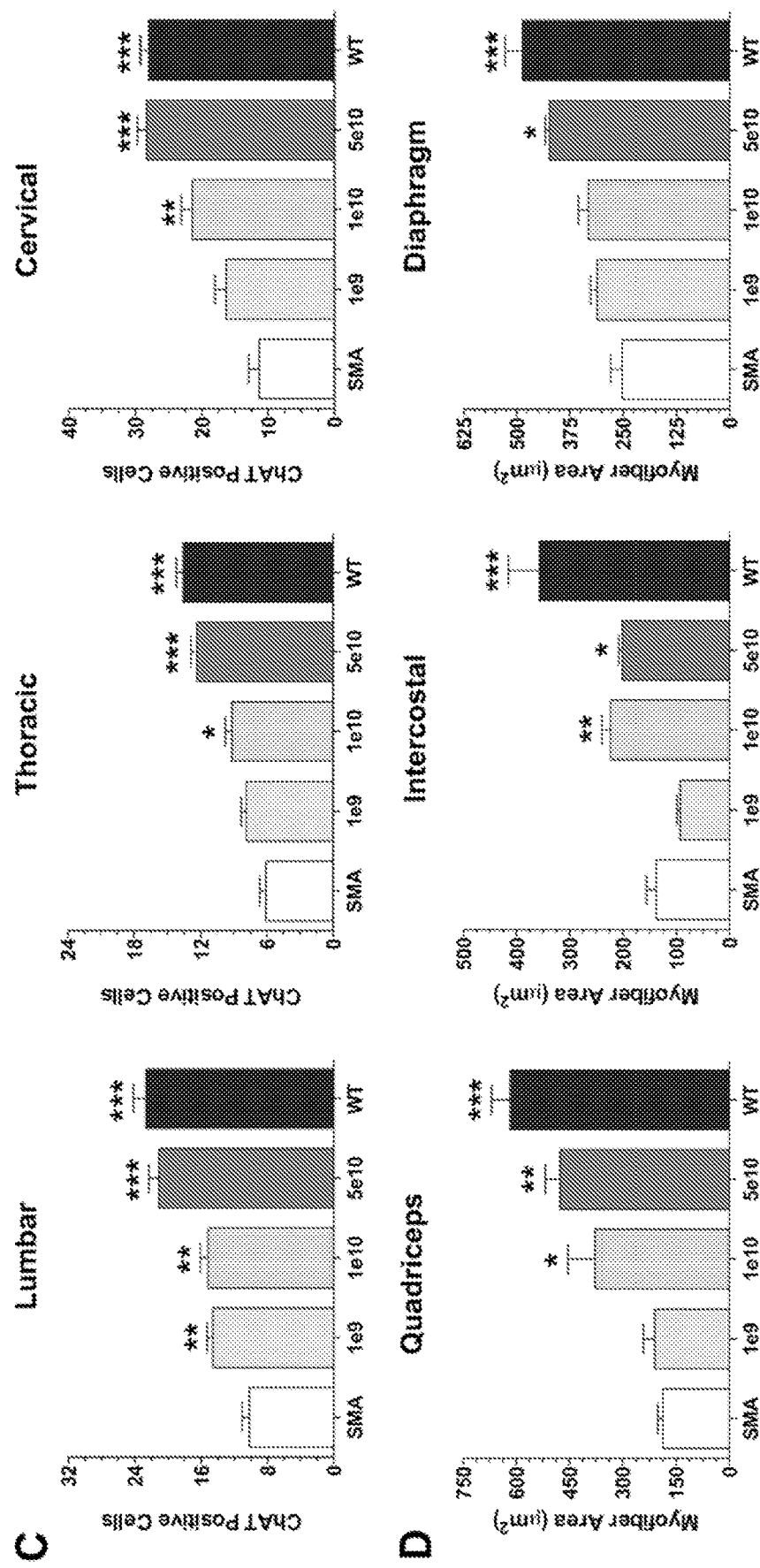
Figure 10:
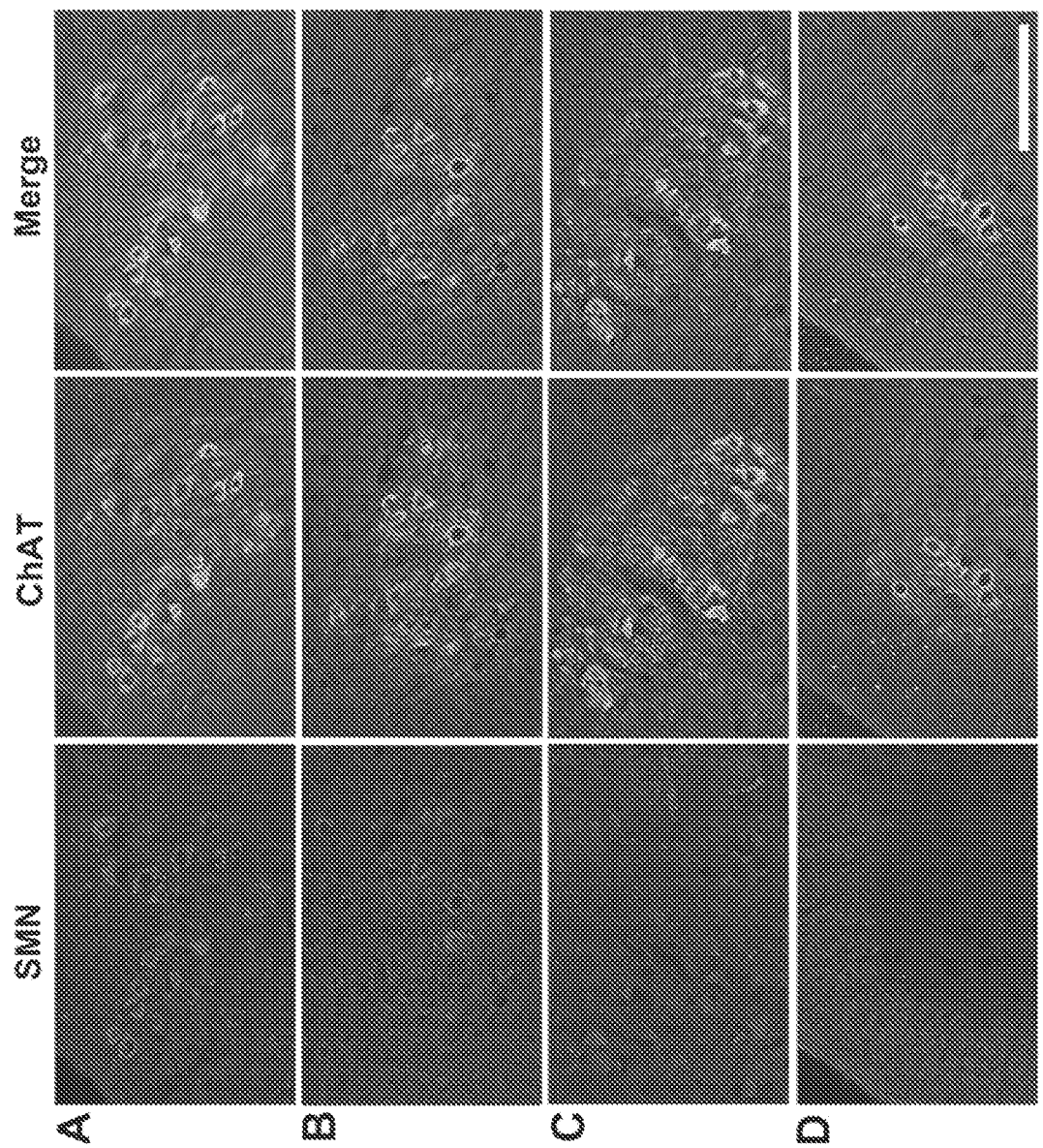
FIG. 10 shows a series of immunohistochemistry images demonstrating the efficiency of scAAV9-hSMN1-mediated transduction of motor neurons in SMA mice. A subset of cells in the ventral horn of the lumbar region stained positively for SMN (left column) and were co-localized in cells that also stained positively for ChAT (middle column) as indicated by the merged picture (right column). A) Sections from animals that had been treated with 5e10 genome copies (gc), B) 1e10 gc and C) 1e9 gc. D) Untreated SMA mice did not contain detectable levels of SMN immuno-positive cells. Scale bar, 0.25 mm.

Western blot analysis of the lumbar, thoracic and cervical cords of SMA mice showed a dose dependent increase in SMN levels. SMA mice injected with 5e10, 1e10 and 1e9 genome copies of scAAV9-hSMN1 generated hSMN levels that were 70-180%, 30-100%, and 10-20% of WT levels, respectively (FIG. 9A). Untreated SMA mice had 10% WT levels of SMN throughout the spinal cord (FIG. 9A). Double immunohistochemical (IHC) staining of tissue sections showed co-localization of hSMN with ChAT in the ventral horn of the spinal cord, indicating that a subset of motor neurons were transduced by the viral vector (FIG. 10). A comprehensive analysis of the number of doubly-stained cells in the lumbar and thoracic regions revealed that motor neuron transduction efficiencies of 30-60%, 10-30%, and <5% were realized with doses of 5e10, 1e10, and 1e9 gc, respectively (FIG. 9B). Irrespective of the dose used, the intensity of the staining for hSMN on cervical tissue sections was very low, which made it difficult to accurately calculate the efficiency of motor neuron transduction in this region (FIG. 9B). Not wishing to be bound by theories, it may be that the absolute levels of hSMN in individual cells in the cervical region approached the limit for detection by immuno-staining but as an aggregate (homogenate) could be detected by the more sensitive Western blot assay.

The efficacy of administering increasing amounts of scAAV9-hSMN1 on the pathological aberrations in the spinal cord and skeletal muscle tissue of SMA mice was also assessed. Analysis of the spinal cord showed that a significantly greater number of motor neurons were observed in the lumbar, thoracic and cervical regions of mice treated with the two highest doses (FIG. 9C). Interestingly, at the dose of 1e10 gc, attainment of 30% WT levels of SMN in the cervical region was associated with an increased number of motor neuron cells (FIGS. 9A, C). Furthermore, in the lumbar region of SMA mice treated with the lowest dose (1e9 gc/mouse), attainment of approximately 20% of WT levels of SMN was sufficient to confer an increased number of motor neurons (FIG. 9A, C). These data indicated that reconstituting SMN levels to ~20-30% WT levels in the spinal cord was sufficient to provide some level of therapeutic benefit in SMA mice.

The quadriceps, intercostal, and diaphragm are skeletal muscles that are innervated by motor neurons originating from the lumbar, thoracic, and cervical regions, respectively. Measurement of the cross-sectional areas of individual myofibers in the quadriceps and intercostal muscles of SMA mice administered the two highest doses showed a significant increase in their size compared to untreated controls (FIG. 9D). In the diaphragm, a significant increase in myofiber size was only noted in the 5e10 gc-treated group. The intercostal muscle at 1e10 gc and the diaphragm muscle at 5e10 both showed a significant increase in myofiber size correlated with 70% SMN levels (FIG. 9A, D). Taken together, the data indicate that reconstituting SMN to ~20-30% of WT levels was sufficient to rescue motor neurons from cell death and increasing SMN levels to ~70% of WT improved muscle physiology (i.e., increasing myofiber size). Measurement of the Extent of Motor Neuron Transduction by scAAV9-hSMN1 Required for Therapeutic Efficacy in SMA Mice.

Figure 11:
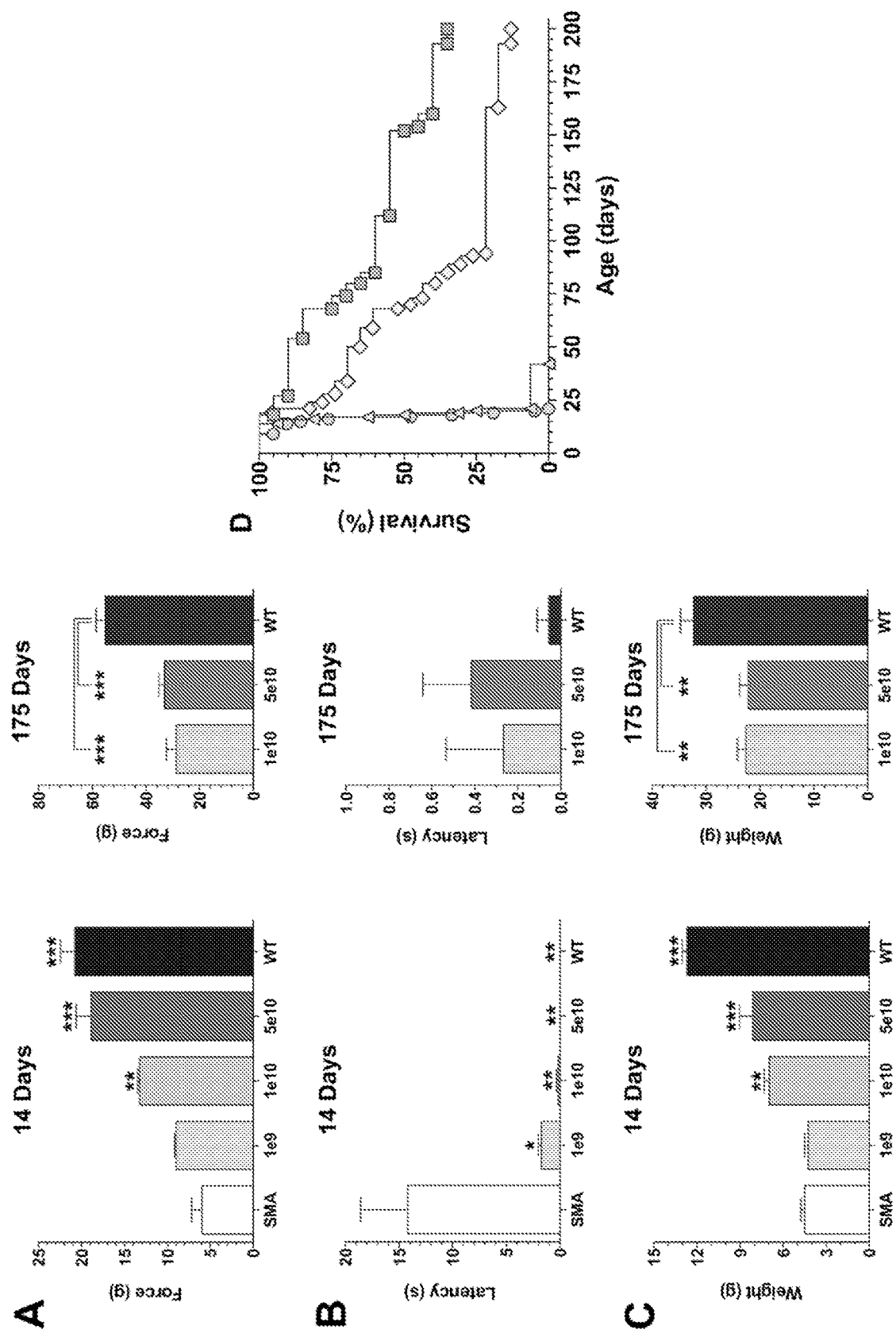
FIG. 11 shows the effect of viral dose on motor function and survival in SMA mice. Graphs showing A) measurements of grip strengths, B) righting reflexes, and C) body weights, at 14 days (left column) and 175 days (right column) post-injection. D) The Kaplan-Meier survival curve showed median survival of 153 days (P<0.0001), 70 days (P<0.0001), and 18 days (P>0.05) for SMA mice treated with doses of 5e10 gc (n=20), 1e10 gc (n=23), 1e9 gc (n=16) of scAAV9-hSMN1, respectively. Control SMA mice treated with matched volumes of saline (n=21) produced a median survival of 17 days. Statistics: $*p<0.05$; $p<0.01$; $*p<0.001$.

Animals administered increasing amounts of scAAV9-hSMN1 were also monitored for their effects on function and survival. The grip strength and righting reflex tests of SMA mice administered the two highest doses showed significant and sustained improvements in muscle strength and coordination when tested at day 14 and 175 (FIG. 11A, B). Mice administered the two highest doses also showed significant increases in body weight when compared to those treated with the lowest dose (1e9 gc) or untreated controls (FIG. 11C). Importantly, treatment with scAAV9-hSMN1 resulted in a remarkable increase in the median lifespans of the SMA mice (FIG. 11D). Animals administered 5e10, 1e10 and 1e9 gc exhibited median lifespans of 153 days (+800% increase compared to saline controls, $p<0.0001$), 70 days (+300%, $p<0.0001$), and 18 days (+6%, $p=0.1329$), respectively (FIG. 11D). A dose of 1e10 gc was sufficient to promote a significant extension in longevity, which correlated with attainment of a minimum of 10-30% motor neuron transduction (FIG. 9B) and 30-70% of WT levels of SMN in SMA mice (FIG. 9A). About 10-30% motor neuron transduction was selected as a benchmark criterion for success in intrathecal delivery studies in large animal models.

Fidelity of Intrathecal Injection of scAAV9-hSMN1 at Transducing the Requisite Number of Motor Neurons in Juvenile Farm Pigs for Efficacy.

Figure 12:
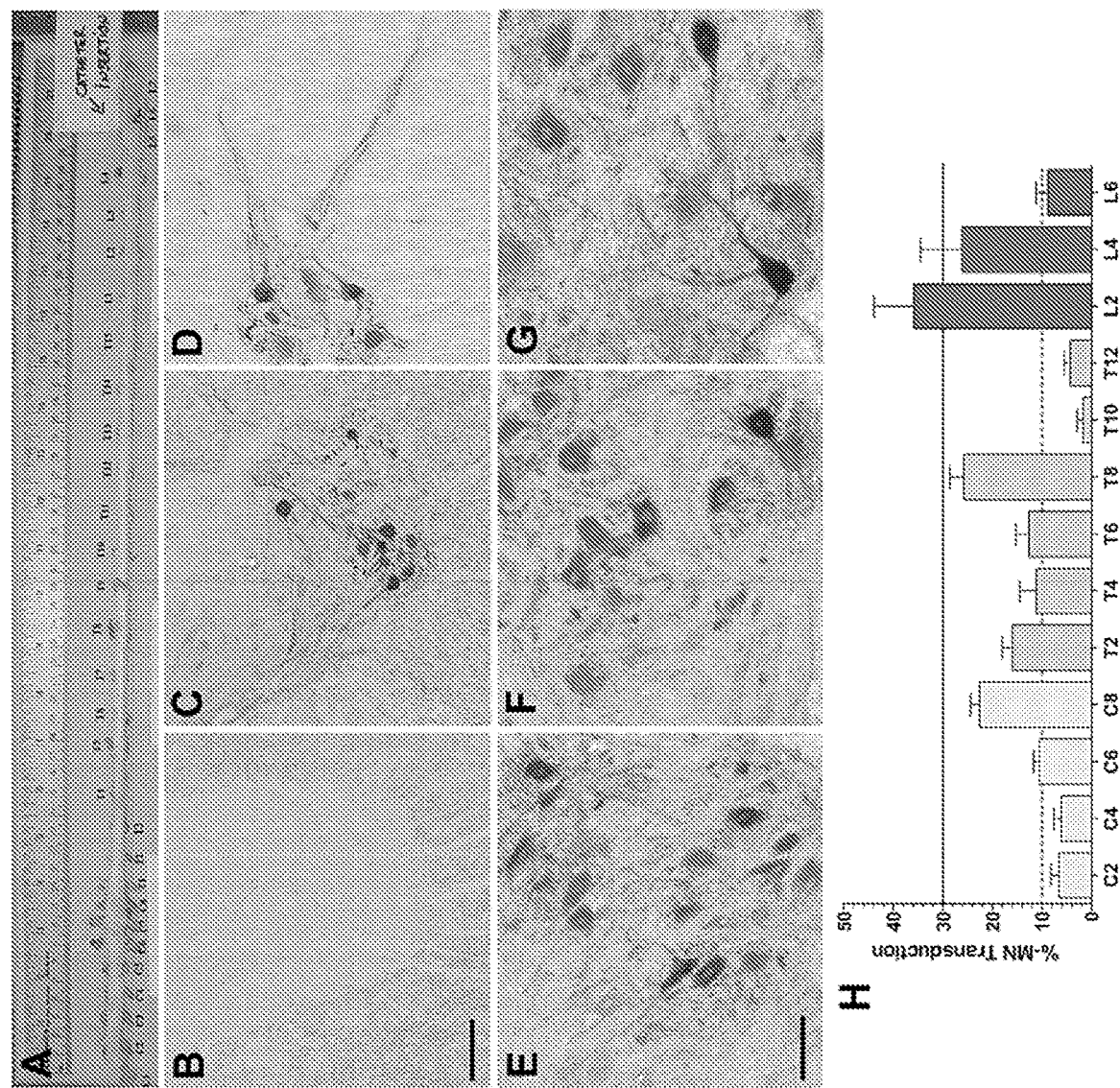
FIG. 12 shows intrathecal delivery of scAAV9-eGFP into juvenile farm pigs. A) At 35 days post-treatment with either saline or scAAV9-eGFP, the pig spinal cord was dissected in its entirety and each segment identified. B) Analysis of lumbar segment 2 (L2) from the saline-treated pig showed no GFP expression. C and D) In contrast, scAAV9-eGFP treated pigs showed robust expression of GFP in the ventral horn, as exemplified by C) L2 and D) cervical segment 8 (C8). E-G) Double IHC staining with ChAT showed a co-localization of GFP with ChAT signal in E) C8, F) thoracic segment 8 (T8), and G) L2. H) A comprehensive analysis of the double-labeled cells along the rostro-caudal axis of the spinal cord showed that many of the segments had 10-30% motor neuron transduction. Scale bars: 0.2 mm (B-D), 0.1 mm (E-G).

Intrathecal administration of a scAAV9-eGFP vector in larger animals was evaluated. The pig was chosen as one of the large animal species because the size and morphology of its spinal cord closely resembles that of humans, making it a reliable model for translational research of neurosurgical approaches to the spinal cord (Federici et al 2012). Juvenile farm pigs were injected with scAAV9-eGFP (n=2) or saline (n=1) into the intrathecal (IT) space to determine if widespread motor neuron transduction could be achieved in a large spinal cord. A laminectomy was performed on L5 and a catheter was threaded to the C8 segment at which juncture 1e12 gc of scAAV9-eGFP in a volume of 0.5 ml was injected. The catheter was then retracted back to approximately the T8 segment and another 1e12 gc of scAAV9-eGFP was administered, and then retracted once again to approximately the L2 segment where a third deposit of 1e12 gc of the viral vector was made. Thus, each pig received a total of 3e12 gc of scAAV9-eGFP in a volume of 1.5 ml. The animals were sacrificed at 35 days post-injection and the different sections of the spinal cord were identified and dissected (FIG. 12A). Abundant GFP-positively stained cells were observed in the ventral horns of the spinal cords of pigs treated with scAAV9-eGFP but not with saline (FIG. 12B-D).

The size and location of the GFP-positive cell bodies in the ventral horn were consistent with motor neuron transduction. However, to confirm the identity of the GFP-positive cells and to calculate the percentage of motor neurons transduced by scAAV9-eGFP, double IHC was performed on every other spinal cord segment between C2 and L6. As illustrated by the segments C8, T8, and L2, a number of cells showed co-staining with GFP and ChAT indicating that a subset of transduced cells were indeed motor neurons (FIG. 12E-G). A comprehensive analysis of the entire spinal cord showed that >10% of motor neurons were transduced in the majority of the segments (FIG. 12H). In some segments, >30% of the motor neurons were transduced by scAAV-eGFP (FIG. 12H). Thus, intrathecal injection of recombinant AAV vectors into cerebrospinal fluid of juvenile pigs, which are approximate to the size of young humans, support the minimal level of motor neuron transduction shown necessary for efficacy in SMA mice.

Fidelity of Intrathecal Injection of scAAV9-hSMN1 at Transducing the Requisite Number of Motor Neurons in Juvenile Monkeys for Efficacy.

To determine whether widespread motor neuron transduction could be achieved in a large animal model that more closely resemble young human infants, juvenile cynomolgus monkeys were injected with scAAV9-eGFP into the intrathecal space. However, unlike the pig injections where a catheter was threaded through the IT space, the viral vector was injected directly into the cisterna magna and the lumbar subarachnoid space of the non-human primate (NHP). The selection of this approach was an attempt to eliminate the potential for catheter entanglement during the threading process. One cohort of monkeys (n=3) received 3 ml (1.25e13 gc) of scAAV9-eGFP into the lumbar subarachnoid space and another 3 ml (1.25e13 gc) into the cisterna magna for a total of 6 ml (2.5e13 gc) per monkey. A second cohort of monkeys was injected with 3 ml (1.25e13 gc) of scAAV9-eGFP into the cisterna magna alone to determine if widespread gene delivery could be achieved with a single injection. All monkeys were sacrificed at 30 days post-injection.

Figure 13:
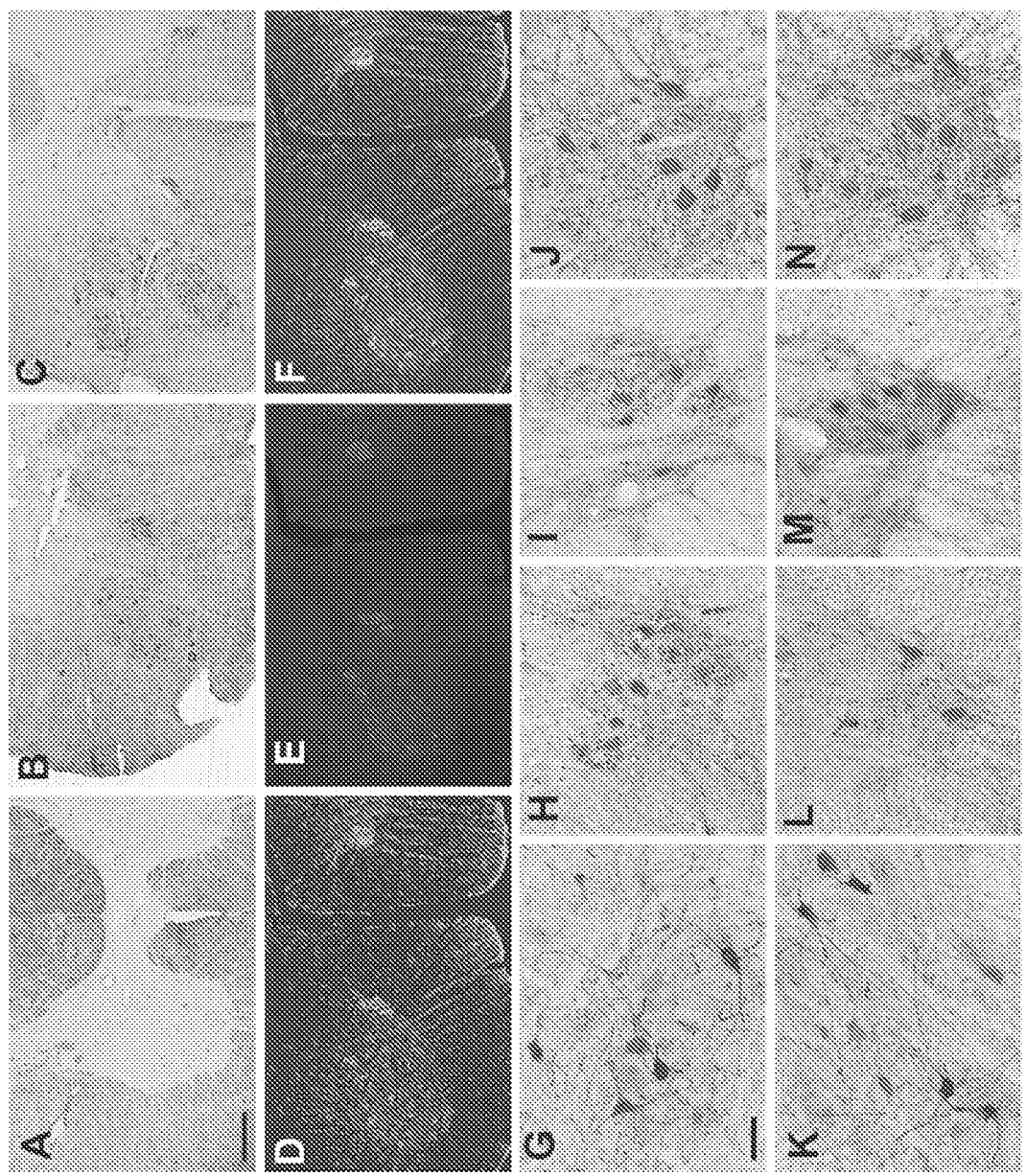
FIG. 13 shows intrathecal delivery of scAAV9-eGFP into juvenile cynomolgus monkeys. A) Analysis of frozen tissue sections from animals administered saline did not produce detectable GFP staining. In contrast, monkeys treated with either a combination of B) cisterna magna and lumbar injections or C) cisterna magna alone injections of scAAV9-eGFP resulted in robust GFP staining in the ventral horn of lumbar segment 6. Double IHC for D) GFP and E) ChAT showed robust co-localization of signal in large cell bodies of the ventral horn of L6. Robust GFP expression was observed throughout the ventral horn of the spinal cord as evidenced by (G and K) cervical segment 6, (H and L) thoracic segment 3, (I and M) lumbar segment 1, and (J and N) sacral segment 2 of monkeys that received either (G-J) the combination cisterna magna and lumbar or (K-N) cisterna magna alone injections. O) A comprehensive quantitation showed motor neuron transduction efficiencies of between 15 and 50% in monkeys treated by cisterna magna injections alone. P) This value was greater in animals treated with the combination cisterna magna and lumbar injections, which showed a motor neuron transduction rate of 25-75%. Scale bars: 0.5 mm (A-F), 0.1 mm (H-N).
Figure 13:
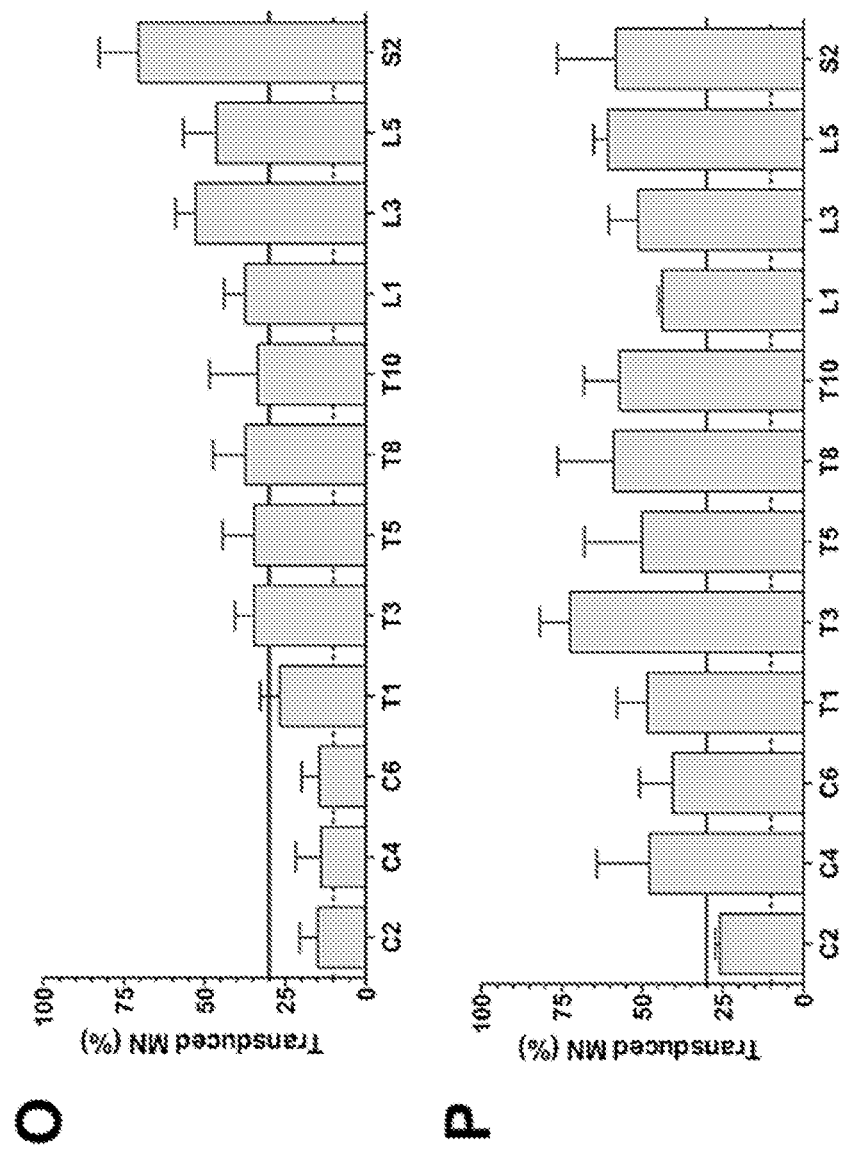

Analysis of tissue sections from both cohorts of monkeys magna showed similar, robust expression of GFP in the lumbar ventral horn (FIG. 13A-C). Co-staining for GFP and ChAT confirmed that a subset of the transduced cells were motor neurons (FIG. 13D-F). Transduction of motor neurons was also evident in other regions of the spinal cord including the cervical, thoracic and sacral segments (FIG. 13G-N). A comprehensive analysis of the monkeys treated by the combination of lumbar and cisterna magna injections showed 25-75% motor neuron transduction in all segments analyzed (FIG. 13P). Animals treated by cisterna magna injections resulted in 15-50% motor neuron transduction throughout the cervical, thoracic, and lumbar segments (FIG. 13O). Not wishing to be bound by any theories, the increased motor neuron transduction rate in the combination lumbar and cisterna magna group might have been due to delivery of a larger dose of the vector to these animals.

Figure 14:
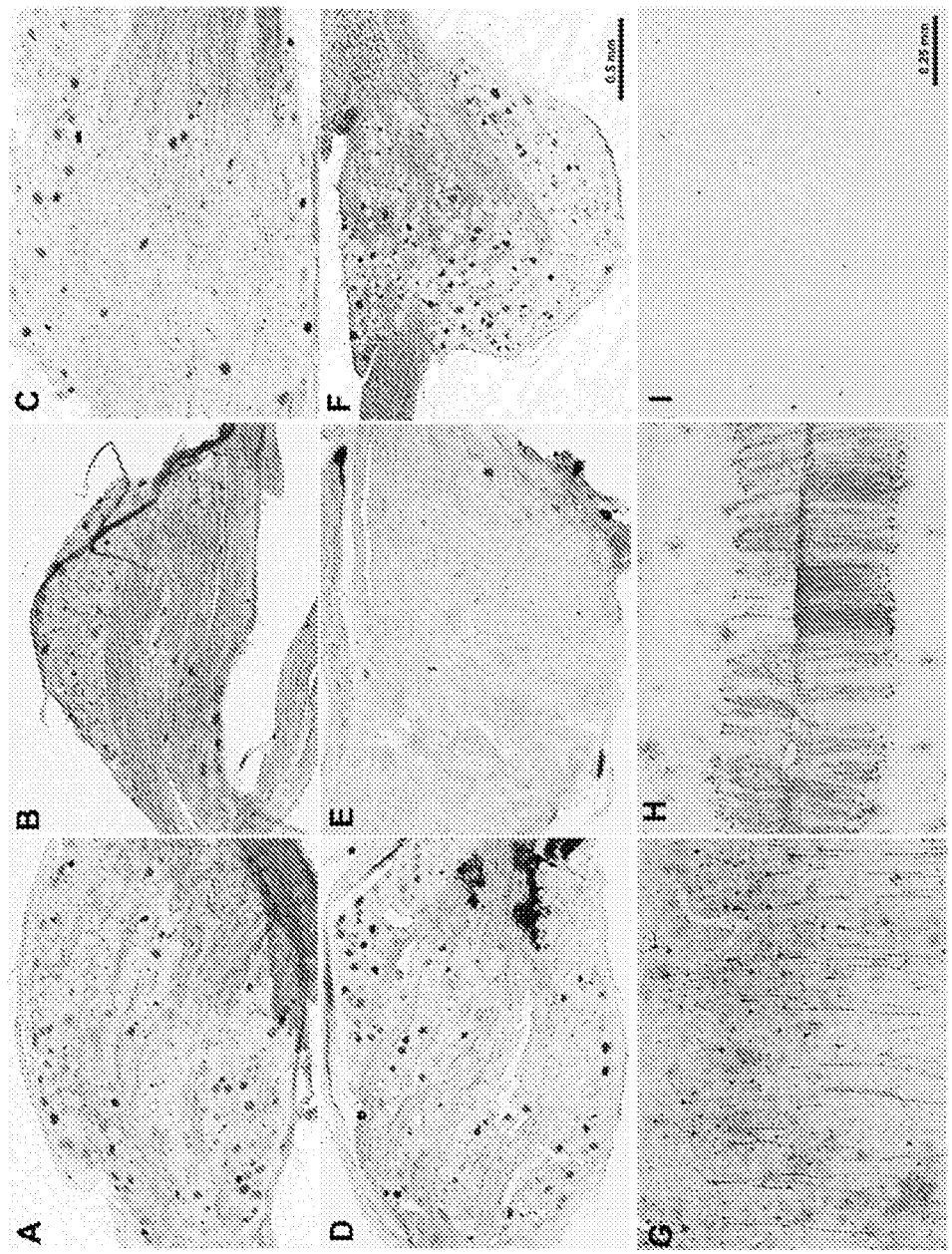
FIG. 14 shows that intrathecal delivery of scAAV9-eGFP into monkeys resulted in transduction of dorsal root ganglia and brain. Shown are the (A, D) dorsal root ganglia of the cervical, (B, E) thoracic, and (C, F) lumbar segments from animals treated by (A-C) the combination cisterna magna and lumbar injections or (D-F) cisterna magna alone. (G, H) Positive GFP immuno-staining was also observed in the brain of both treatment groups, especially in the cerebral cortex and cerebellum. G-I) A representative sample showing GFP expression (G) in the cerebral cortex of monkeys treated by the combination protocol and (H) in the cerebellum of monkeys treated by cisterna magna alone. I) The saline treated monkey was negative for GFP expression. Scale bars: 0.5 mm (A-F), 0.25 mm (G-I).

Other regions of the CNS were also transduced following intrathecal delivery of scAAV9-eGFP. The dorsal root ganglia (DRG) were genetically modified (as evidenced by expression of GFP) in both treatment cohorts (FIG. 14A-F). Furthermore, GFP-positive pyramidal neurons and glia cells were detected along the cerebral cortex that spanned the pre-frontal to the occipital cortices in both treatment cohorts (FIG. 14G, I). Purkinje cells throughout the cerebellar cortex were also efficiently transduced in both cohorts (FIG. 14H, I). Overall, the pattern of GFP expression in the DRG and brain was similar between the two groups. GFP expression on tissue sections was not detected in the liver and spleen of the monkeys suggesting that the amount of scAAV9-eGFP that entered the systemic circulation was low. The levels of antibodies against the AAV9 capsid in the serum and CSF were monitored. Baseline levels of pre-existing neutralizing antibodies (NAB) to AAV9 in the serum in all the monkeys were low (Table 1). At 30 days post-injection, the serum and CSF levels of anti-AAV9 NAB were significantly higher (Table 1).

The results describe herein, indicate that intrathecal injection of recombinant AAV vectors into the cisterna magna and lumbar subarachnoid space in juvenile monkeys support the level of motor neuron transduction shown to be efficacious in SMA mice.

TABLE 1

NAB against AAV9 in NHPs.

| NHP ID | Group | Dose (gc) | Anti-AAV9 NAB Titer in Serum (Baseline) | Anti-AAV9 NAB Titer in Serum (30 d Post-inj) | Anti-AAV9 NAB Titer in CSF (Baseline) | Anti-AAV9 NAB Titer in CSF (30 d Post-inj) |
|---|---|---|---|---|---|---|
| 39318 | CM + Lumbar | 2.50e13 | <4 | 16384 | <4 | 512 |
| 39334 | CM + Lumbar | 2.50e13 | <4 | 4096 | <4 | 32 |
| 39537 | CM + Lumbar | 2.50e13 | <4 | 2048 | <4 | 4 |
| 40370 | CM | 1.25e13 | 32 | 16384 | <4 | 2048 |
| 39525 | CM | 1.25e13 | <4 | 8192 | <4 | 512 |
| 39583 | CM | 1.25e13 | 4 | 16384 | <4 | 2048 |

NAB, neutralizing antibody;
CM, cisterna magna;
CSF cerebral spinal fluid.

Bennett, J. (2010). Safety and efficacy of subretinal readministration of a viral vector in large animals to treat congenital blindness. Sci Transl. Med. 2, e21ra16.

Avila A M, Burnett B G, Taye A A, Gabanella F, Knight M A, Hartenstein P, Cizman Z, Di Prospero N A, Pellizzoni L, Fischbeck K H, Sumner C J. (2007). Trichostatin A increases SMN expression and survival in a mouse model of spinal muscular atrophy. J Clin Invest 117:659-671.

Bankiewicz, K. S., Forsayeth, J., Eberling, J. L., Sanchez-Pernaute, R., Pivirotto, P., Bringas, J., Herscovitch, P., Carson, R. E., Eckelman, W., Reutter, B., and Cunningham, J. (2006). Long-term clinical improvement in MPTP-lesioned primates after gene therapy with AAV-hAADC. Mol. Ther. 14, 564-570.

Bebee, T. W., Dominguez, C. E., and Chandler, D. S. (2012). Mosue models of SMA: tools for disease characterization and therapeutic development. Hum. Genet. 131, 1277-1293.

Bevan, A. K., Duque, S., Foust, K. D., Morales, P. R., Braun, L., Schmelzer, L., Chan, C. M., McCrate, M., Chicoine, L. G., Coley, B. D., Porensky, P. N., Kolb, S. J., Mendell, J. R., Burghes, A. H., and Kaspar, B. K. (2011). Systemic gene delivery in large species for targeting spinal cord, brain, and peripheral tissues for pediatric disorders. Mol. Ther. 19, 1971-1980.

Boutin, S., Monteilhet, V., Veron, P., Leborgne, C., Benveniste, O., Montus, M. F., and Masurier, C. (2010). Prevalence of serum IgG and neutralizing factors against adeno-associated virus (AAV) types 1, 2, 5, 6, 8, and 9 in the healthy population: implications for gene therapy using AAV vectors. Hum. Gene Ther. 21, 704-712.

Bowerman M, Murray L M, Beauvais A, Pinheiro B, Kothary R (2012) A critical smn threshold in mice dictates onset of an intermediate spinal muscular atrophy phenotype associated with a distinct neuromuscular junction pathology. Neuromuscul. Disord. 22:263-276.

Butchbach M E, Singh J, Thorsteinsdóttir M, Saieva L, Slominski E, Thurmond J, Andrésson T, Zhang J, Edwards J D, Simard L R, Pellizzoni L, Jarecki J, Burghes A H, Gurney M E. (2010) Effects of 2,4-diaminoquinazoline derivatives on SMN expression and phenotype in a mouse model for spinal muscular atrophy. Hum Mol Genet. 19:454-467.

REFERENCES

A D., Mingozzi, F., Hui, D., Bennicelli, J. L., Wei, Z., Chen, Y., Bote, E., Grant, R. L., Golden, J. A., Narfstrom, K., Syed, N. A., Orlin, S. E., High, K. A., Maguire, A. M., and Chen, T. H. et al. (2010). Randomized, double-blind, placebo-controlled trial of hydroxyurea in spinal muscular atrophy. Neurology 75, 2190-2197.

Dominguez E, Marais T, Chatauret N, Benkhelifa-Ziyyat S, Duque S, Ravassard P, Carcenac R, Astord S, Pereira de Moura A, Voit T, Barkats M. (2011) Intravenous scAAV9 delivery of a codon-optimized SMN1 sequence rescues SMA mice. Hum. Mol. Genet. 20, 681-693.

Duque S, Joussemet B, Riviere C, Marais T, Dubreil L, Douar A M, Fyfe J, Moullier P, Colle M A, Barkats M. (2009) Intravenous administration of self-complementary AAV9 enables transgene delivery to adult motor neurons. Mol. Ther. 17, 1187-1196.

Farooq, F., Molina, F. A., Hadwen, J., MacKenzie, D., Witherspoon, L., Osmond, M., Holcik, M., and MacKenzie, A. (2011). Prolactin increases SMN expression and survival in a mouse model of severe spinal muscular atrophy via the STAT5 pathway. J. Clin. Invest. 121, 3042-3050.

Federici, T., Taub, J. S., Baum, G. R., Gray, S. J., Grieger, J. C., Matthews, K. A., Handy, C. R., Passini, M. A., Samulski, R. J., and Boulis, N. M. (2012). Robust spinal motor neuron transduction following intrathecal delivery of AAV9 pigs. Gene Ther. 19, 852-859.

Foust, K. D. et al. (2010) Rescue of the spinal muscular atrophy phenotype in a mouse model by early postnatal delivery of SMN. Nat. Biotech. 28, 271-274.

Garbes L, Riessland M, Milker I, Heller R, Hauke J, Trankle C, Coras R, Blümcke I, Hahnen E, Wirth B. (2009) LBH589 induces up to 10-fold SMN protein levels by several independent mechanisms and is effective even in cells from SMA patients non-responsive to valproate. Hum Mol Genet. 18:3645-3658.

Gray S J, Matagne V, Bachaboina L, Yadav S, Ojeda S R, Samulski R J (2011) Preclinical differences of intravascular AAV9 delivery to neurons and glia: a comparative study of adult mice and nonhuman primates. Mol Ther 19:1058-1069.

Gray S J, Kalburgi S N, McCown T J, Samulski R J (2013) Global CNS gene delivery and evasion of anti-AAV-neutralizing antibodies by intrathecal AAV administration in non-human primates. Gene Therapy. Doi:10.1038/gt.2012.101.

Hamilton, G., and Gillingwater, T. H. (2012) Spinal muscular atrophy: going beyond the motor neuron. Trends Mol. Med. (in press).

Heier, C. R., and DiDonato, C. J. (2009). Translational readthrough by the aminoglycoside geneticin (G418) modulated SMN stability in vitro and improves motor function in SMA mice in vivo. Hum. Mol. Genet. 18, 1310-1322.

Hua, Y., et al., (2008). Antisense masking of an hnRNP A1/A2 intronic splicing silencer corrects SMN2 splicing in transgenic mice. Am. J. Hum. Genet. 82, 834-848.

Hua Y, Sahashi K, Hung G, Rigo F, Passini M A, Bennett C F, Krainer A R. (2010). Antisense correction of SMN2 splicing in the CNS rescues necrosis in a type III SMA mouse model. Genes Dev 24:1634-1644.

Hua Y, Sahashi K, Rigo F, Hung G, Horev G, Bennett C F, Krainer A R. (2011) Peripheral SMN restoration is essential for long-term rescue of a severe spinal muscular atrophy mouse model. Nature 478:123-126.

Kolb, S. J., and Kissel, J. T. (2011) Spinal muscular atrophy: a timely review. Arch. Neurol. 68, 979-984.

Kole, R., Krainer, A. R., and Altman, S. (2012). RNA therapeutics: beyond RNA interference and antisense oligonucleotides. Nature Rev. Drug Dis. 11, 125-140.

Le, T. T. et al. (2005) SMNΔ7, the major product of the centromeric survival motor neuron (SMN2) gene, extends survival in mice with spinal muscular atrophy and associates with full-length SMN. Hum Mol. Genet. 14, 845-857.

Lefebvre, S. et al. (1995). Identification and characterization of a spinal muscular atrophy-determining gene. Cell 80, 155-165.

Lewelt, A., Newcomb, T. M., and Swoboda, K. J. (2012). New therapeutic approaches to spinal muscular atrophy. Curr. Neurol. Neurosci. Rep. 12, 42-53.

Lorson, M. A., Spate, L. D., Samuel, M. S., Murphy, C. N., Lorson, C. L., Prather, R. S., and Wells, K. D. (2011). Disruption of the survival motor neuron (SMN) gene in pigs using ssDNA. Transgenic Res. 20, 1293-1304.

Markowitz, J. A., Singh, P., and Darras, B. T. (2012). Spinal muscular atrophy: a clinical and research update. Ped. Neurol. 46, 1-12.

Mattis, V. B., Ebert, A. D., Fosso, M. Y., Chang, C. W., and Lorson, C. L. (2009). Delivery of a read-through inducing compound, TC007, lessens the severity of a spinal muscular atrophy animal model. Hum. Mol. Genet. 18, 3906-3913.

Mercuri, E. et al (2007). Randomized, double blind, placebo-controlled trial of phenylbutyrate in spinal muscular atrophy. Neurology 68, 51-55.

Monani, U. R., Lorson, C. L., Parsons, D. W., Prior, T. W., Androphy, E. J., Burghes, A. H., and McPherson, J. D. (1999). A single nucleotide difference that alters splicing patterns distinguishes the SMA gene SMN1 from the copy gene SMN2. Hum. Mol. Genet. 8, 1177-1183.

Nathwani, A. C. et al. (2011). Adenovirus-associated virus vector-mediated gene transfer in hemophilia B. N. Engl. J. Med. 365, 2357-2365.

Passini, M. A. et al. (2010) CNS-targeted gene therapy improves survival and motor function in a mouse model of spinal muscular atrophy. J. Clin. Invest. 120, 1253-1264.

Passini, M. A. and Cheng, S. H. (2011a). Prospects for the gene therapy of spinal muscular atrophy. Trends Mol. Med. 17, 259-265.

Passini, M. A., et al. (2011b). Antisense oligonucleotides delivered to the mouse CNS ameliorate symptoms of severe spinal muscular atrophy. Sci. Transl. Med. 3, 72ra18

Samaranch, L., Salegio, E. A., Sebastian, W. S., Kells, A. P., Foust, K. D., Bringas, J. R., Lamarre, C., Forsayeth, J., Kaspar, B. K., and Bankiewicz, K. S. (2012). Adeno-associated virus serotype 9 transduction in the central nervous system of nonhuman primates. Hum. Gene Ther. 23, 382-389.

Singh, N. K., et al. (2006). Splicing of a critical exon of human survival motor neuron is regulated by a unique silencer element located in the last intron. Mol. Cell. Biol. 26, 1333-1346.

Sumner, C. J. et al. (2003). Valproic acid increases SMN levels in spinal muscular atrophy patient cells. Ann. Neurol. 54, 647-654.

Treleaven, C. M., Tamsett, T. J., Bu, J., Fidler, J. A., Sardi, S. P., Hurlbut, G. D., Woodworth, L. A., Cheng, S. H., Passini, M. A., Shihabuddin, L. S., and Dodge, J. C. (2012). Gene transfer to the CNS is efficacious in immune-primed mice harboring physiologically relevant titers of anti-AAV antibodies. Mol. Ther. 20, 1713-1723.

Valori C F, Ning K, Wyles M, Mead R J, Grierson A J, Shaw P J, Azzouz. (2010) Systemic delivery of scAAV9 expressing SMN prolongs survival in a model of spinal muscular atrophy Sci Transl Med. 2:35ra42.

What is claimed is:

1. A method for treating spinal muscular atrophy in a primate with spinal muscular atrophy, comprising administering via intracisternal injection to the cisterna magna of the primate at least $1.25 \times 10^{13}$ genome copies of a recombinant adeno-associated virus (rAAV) viral particle comprising a vector encoding a primate SMN and administering via direct injection into the spinal cord at of the primate at least $1.25 \times 10^{13}$ genome copies of a recombinant adeno-associated virus (rAAV) viral particle comprising a vector encoding a primate SMN; wherein the rAAV viral particle comprises an AAV9 serotype capsid.

2. A method for ameliorating a symptom of spinal muscular atrophy in a primate, comprising administering via intracisternal injection to the cisterna magna of the primate at least $1.25 \times 10^{13}$ genome copies of a recombinant adeno-associated virus (rAAV) viral particle comprising a vector encoding a primate SMN and administering via direct injection into the spinal cord at of the primate at least $1.25 \times 10^{13}$ genome copies of a recombinant adeno-associated virus (rAAV) viral particle comprising a vector encoding a primate SMN, wherein the rAAV viral particle comprises an AAV9 serotype capsid.

3. The method of claim 2, wherein the symptom of spinal muscular atrophy is one or more of muscle wasting, inability to achieve motor milestones, inability to sit, inability to walk, paralysis, respiratory dysfunction, bulbar dysfunction, motor neuron cell loss and neuromuscular junction pathology.

4. A method for delivering a heterologous transgene encoding a primate SMN in a motor neuron in a primate with spinal muscular atrophy, comprising administering via intracisternal injection to the cisterna magna of the primate at least $1.25 \times 10^{13}$ genome copies of a recombinant adeno-associated virus (rAAV) viral particle comprising a vector encoding a primate SMN and administering via direct injection into the spinal cord at of the primate at least $1.25 \times 10^{13}$ genome copies of a recombinant adeno-associated virus (rAAV) viral particle comprising a vector encoding a primate SMN; wherein the rAAV viral particle comprises an AAV9 serotype capsid.

5. The method of claim 4, wherein at least 10-30% of the motor neurons in the lumbar, thoracic and cervical regions of the spinal cord are transduced and/or wherein at least 30% of SMN wild type levels are generated throughout the spinal cord.

6. The method of claim 4, wherein at least $3.5 \times 10^{11}$ genome copies per kg body weight, at least $3.5 \times 10^{12}$ genome copies per kg body weight, at least $5 \times 10^{12}$ genome copies per kg body weight, or at least $5 \times 10^{13}$ genome copies per kg body weight of rAAV is administered to the primate.

7. The method of claim 4, wherein the vector comprises AAV1, AAV2, AAV3, AAV4, AAV5, AAV6, AAV7, AAV8, AAVrh8, AAV9, AAV10, AAVrh10, AAV11, or AAV12 serotype inverted terminal repeats (ITRs).

8. The method of claim 4, wherein the rAAV viral particle comprises an AAV-9 capsid, and wherein the vector comprises AAV2 ITRs.

9. The method of claim 4, wherein the vector is a self-complimenting vector.

10. The method of claim 4, wherein the vector encodes a SMN-1 transgene is operably linked to a promoter.

11. The method of claim 10, wherein the promoter is capable of expressing the SMN-1 transgene in neurons of the spinal cord.

12. The method of claim 11, wherein the promoter comprises a human β-glucuronidase promoter or a cytomegalovirus enhancer linked to a chicken β-actin promoter.

13. The method of claim 4, wherein the vector comprises a polynucleotide encoding the amino acid sequence of SEQ ID NO: 1.

14. The method of claim 4, wherein the primate is a human.

15. The method of claim 14, wherein the human is a pediatric subject or a young adult.

16. The method of claim 4, wherein the rAAV viral particle is in a pharmaceutical composition.

17. The method of claim 1, wherein the administering via direct injection into the spinal cord comprises administering via direct injection into one or more intrathecal spaces in the spinal cord.

18. The method of claim 2, wherein the administering via direct injection into the spinal cord comprises administering via direct injection into one or more intrathecal spaces in the spinal cord.

19. The method of claim 4, wherein the administering via direct injection into the spinal cord comprises administering via direct injection into one or more intrathecal spaces in the spinal cord.

\* \* \* \* \*

UNITED STATES PATENT AND TRADEMARK OFFICE
CERTIFICATE OF CORRECTION

Page 1 of 1

PATENT NO. : 10,821,154 B2
APPLICATION NO. : 14/888385
DATED : November 3, 2020
INVENTOR(S) : Marco A. Passini et al.

It is certified that error appears in the above-identified patent and that said Letters Patent is hereby corrected as shown below:

On the Title Page

In the Abstract

Item (57), Lines 1-2 please replace: "The present provides methods for treating spinal muscular atrophy" with --The present invention provides methods for treating spinal muscular atrophy--; and Item (57), Lines 4-5 please replace: "In one aspect, the viral particles are administered the spinal column" with --In one aspect, the viral particles are administered in the spinal column--.

In the Claims

In Claim 1, Column 39, Line 46, please replace "into the spinal cord at of the primate" with --into the spinal cord of the primate--;

In Claim 2, Column 39, Line 57, please replace "into the spinal cord at of the primate" with --into the spinal cord of the primate--;

In Claim 4, Column 40, Line 46, please replace "into the spinal cord at of the primate" with --into the spinal cord of the primate--; and In Claim 10, Column 41, Lines 3-4, please replace "wherein the vector encodes a SMN-1 transgene is operably linked to a promoter." with --wherein the vector encodes a SMN-1 transgene that is operably linked to a promoter.--.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 7

<210> SEQ ID NO 1
<211> LENGTH: 294
<212> TYPE: PRT
<213> ORGANISM: Homo sapiens

<400> SEQUENCE: 1

```
Met Ala Met Ser Ser Gly Gly Ser Gly Gly Val Pro Glu Gln Glu
1               5                   10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
            35                  40                  45

Ser Phe Lys His Ala Leu Lys Asn Gly Asp Ile Cys Glu Thr Ser Gly
    50                  55                  60

Lys Pro Lys Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
                100                 105                 110

Ile Ala Ser Ile Asp Phe Lys Arg Glu Thr Cys Val Val Val Tyr Thr
            115                 120                 125

Gly Tyr Gly Asn Arg Glu Glu Gln Asn Leu Ser Asp Leu Leu Ser Pro
        130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
                180                 185                 190

Phe Leu Pro Pro Pro Pro Met Pro Gly Pro Arg Leu Gly Pro Gly
            195                 200                 205

Lys Pro Gly Leu Lys Phe Asn Gly Pro Pro Pro Pro Pro Pro Pro
        210                 215                 220

Pro Pro His Leu Leu Ser Cys Trp Leu Pro Pro Phe Pro Ser Gly Pro
225                 230                 235                 240

Pro Ile Ile Pro Pro Pro Pro Ile Cys Pro Asp Ser Leu Asp Asp
                245                 250                 255

Ala Asp Ala Leu Gly Ser Met Leu Ile Ser Trp Tyr Met Ser Gly Tyr
            260                 265                 270

His Thr Gly Tyr Tyr Met Gly Phe Arg Gln Asn Gln Lys Glu Gly Arg
        275                 280                 285

Cys Ser His Ser Leu Asn
        290
```

<210> SEQ ID NO 2
<211> LENGTH: 885
<212> TYPE: DNA
<213> ORGANISM: Homo sapiens

<400> SEQUENCE: 2
atggcgatga gcagcggcgg cagtggtggc ggcgtcccgg agcaggagga ttccgtgctg     60
ttccggcgcg gcacaggcca gagcgatgat tctgacattt gggatgatac agcactgata    120

| | | |
|---|---|---|
| aaagcatatg ataaagctgt ggcttcattt aagcatgctc taaagaatgg tgacatttgt | 180 | |
| gaaacttcgg gtaaaccaaa aaccacacct aaaagaaaac ctgctaagaa gaataaaagc | 240 | |
| caaaagaaga atactgcagc ttccttacaa cagtggaaag ttggggacaa atgttctgcc | 300 | |
| atttggtcag aagacggttg catttaccca gctaccattg cttcaattga ttttaagaga | 360 | |
| gaaacctgtg ttgtggttta cactggatat ggaaatagag aggagcaaaa tctgtccgat | 420 | |
| ctactttccc caatctgtga agtagctaat aatatagaac agaatgctca agagaatgaa | 480 | |
| aatgaaagcc aagtttcaac agatgaaagt gagaactcca ggtctcctgg aaataaatca | 540 | |
| gataacatca agcccaaatc tgctccatgg aactcttttc tccctccacc accccccatg | 600 | |
| ccagggccaa gactgggacc aggaaagcca ggtctaaaat tcaatggccc accaccgcca | 660 | |
| ccgccaccac caccacccca cttactatca tgctggctgc ctccatttcc ttctggacca | 720 | |
| ccaataattc ccccaccacc tcccatatgt ccagattctc ttgatgatgc tgatgctttg | 780 | |
| ggaagtatgt taatttcatg gtacatgagt ggctatcata ctggctatta tatgggtttc | 840 | |
| agacaaaatc aaaaagaagg aaggtgctca cattccttaa attaa | 885 | |

<210> SEQ ID NO 3
<211> LENGTH: 885
<212> TYPE: DNA
<213> ORGANISM: Artificial Sequence
<220> FEATURE:
<223> OTHER INFORMATION: Synthetic construct

<400> SEQUENCE: 3

| | | |
|---|---|---|
| atggctatga gcagtggcgg ctctggcggc ggagtgcctg agcaggaaga tagcgtgctg | 60 | |
| ttcagacggg gcaccggcca gagcgacgac agcgacatct gggatgacac cgccctgatc | 120 | |
| aaggcctacg acaaggccgt ggccagcttc aagcacgccc tgaagaacgg cgatatctgc | 180 | |
| gagacaagcg gcaagcccaa gaccaccccc aagagaaagc ccgccaagaa gaacaagagc | 240 | |
| cagaagaaga ataccgccgc ctccctgcag cagtggaaag tgggcgataa gtgcagcgcc | 300 | |
| atttggagcg aggacggctg catctacccc gccacaatcg ccagcatcga cttcaagcgg | 360 | |
| gaaacctgcg tggtggtgta cacaggctac ggcaacagag aggaacagaa cctgagcgac | 420 | |
| ctgctgagcc ccatctgcga ggtggccaac aacatcgagc agaacgccca ggaaaacgag | 480 | |
| aacgagtccc aggtgtccac cgacgagagc gagaacagca aagcccccgg caacaagagc | 540 | |
| gacaacatca agcctaagag cgccccctgg aacagcttcc tgcctccccc tccaccaatg | 600 | |
| cctggcccta gactgggacc tggcaagccc ggcctgaagt tcaatggccc cctcccccca | 660 | |
| cctccaccac caccccctca tctgctgagc tgttggctgc cccattccc tagcggccct | 720 | |
| cccatcattc ctccaccccc cccaatctgc ccgacagcc tggatgatgc tgatgccctg | 780 | |
| ggctccatgc tgatctcttg gtacatgagc ggctaccaca ccggctacta catgggcttc | 840 | |
| cggcagaacc agaaagaggg ccgctgtagc cacagcctga actga | 885 | |

<210> SEQ ID NO 4
<211> LENGTH: 885
<212> TYPE: DNA
<213> ORGANISM: Artificial Sequence
<220> FEATURE:
<223> OTHER INFORMATION: Synthetic construct

<400> SEQUENCE: 4

| | | |
|---|---|---|
| atggcgatga gcagcggtgg ttccggagga ggggtgccgg agcaggagga ttccgtcctt | 60 | |
| ttcagacggg gaaccggcca gtcggacgac tcggacatct gggatgacac cgcactgatc | 120 | |

```
aaagcatacg ataaagcagt ggcatcgttc aagcacgccc ttaagaatgg agacatttgc    180
gaaaccagcg ggaagccaaa aactactccg aagcgcaagc ccgccaagaa gaataagtca    240
cagaagaaaa acaccgccgc ttcgctgcaa cagtggaaag tgggcgacaa gtgctccgcg    300
atctggtcag aggatggctg catctacccg gccacgatcg cctccatcga cttcaagcgg    360
gaaacttgtg tggtcgtcta cactggctac ggaaaccgcg aggaacagaa tctcagcgat    420
ctcctcagcc cgatttgtga ggtggccaac aatatcgaac agaacgcgca agaaaacgag    480
aacgagtccc aagtgtcgac tgacgaatcg gaaaattcgc gctcaccagg aaacaagtca    540
gataacatca agcccaaaag cgcgccatgg aacagctttt tgccgccacc accacctatg    600
cctggaccga ggctgggacc gggaaagccg ggactcaaat tcaacggccc accgcctccg    660
ccacctccgc ctccacccca cttgctgtcc tgctggctgc cgccatttcc gtcgggtccg    720
cctatcatcc ctcctccacc gccgatttgc cccgactcac tcgacgatgc tgacgccctg    780
gggtcaatgc tgatctcctg gtatatgtcc ggctaccata ccggatacta catgggattc    840
cggcagaacc aaaaggaagg gagatgctcc cattcgctga attga                    885

<210> SEQ ID NO 5
<211> LENGTH: 1860
<212> TYPE: DNA
<213> ORGANISM: Artificial Sequence
<220> FEATURE:
<223> OTHER INFORMATION: Synthetic construct

<400> SEQUENCE: 5
ggccactccc tctctgcgcg ctcgctcgct cactgaggcc gggcgaccaa aggtcgcccg     60
acgcccgggc tttgcccggg cggcctcagt gagcgagcga gcgcgcagag agggagtggc    120
caactccatc actaggggtt cctggagggg tggagtcgtg acagatctga attcctgctg    180
ggaaaagcaa gtggaggtgc tccttgaaga acaggggga tcccaccgat ctcaggggtt    240
ctgttctggc ctgcggccct ggatcgtcca gcctgggtcg gggtggggag cagacctcgc    300
ccttatcggc tggggctgag ggtgagggtc ccgtttcccc aaaggcctag cctggggttc    360
cagccacaag ccctaccggg cagcgcccgg ccccgcccct ccaggcctgg cactcgtcct    420
caaccaagat ggcgcggatg gcttcaggcg catcacgaca ccggcgcgtc acgcgacccg    480
ccctacgggc acctccgcg ctttttcttag cgccgcagac ggtggccgag cggggaccg    540 ggaagcatgg cccgggctgc agctctaagg taaatataaa attttaagt gtataatgtg    600 ttaaactact gattctaatt gtttctctct tttagattcc aacctttgga actcgaattc    660
atggcgatga gcagcggcgg cagtggtggc ggcgtcccgg agcaggagga ttccgtgctg    720
ttccggcgcg gcacaggcca gagcgatgat tctgacattt gggatgatac agcactgata    780
aaagcatatg ataaagctgt ggcttcattt aagcatgctc taaagaatgg tgacatttgt    840
gaaacttcgg gtaaaccaaa accacacct aaaagaaaac ctgctaagaa gaataaaagc    900
caaaagaaga atactgcagc ttccttacaa cagtggaaag ttggggacaa atgttctgcc    960
atttggtcag aagacggttg catttaccca gctaccattg cttcaattga ttttaagaga   1020
gaaacctgtg ttgtggttta cactggatat ggaaatagag aggagcaaaa tctgtccgat   1080
ctactttccc caatctgtga agtagctaat aatatagaac agaatgctca agagaatgaa   1140
aatgaaagcc aagtttcaac agatgaaagt gagaactcca ggtctcctgg aaataaatca   1200
gataacatca agcccaaatc tgctccatgg aactcttttc tccctccacc accccccatg   1260
```

```
ccagggccaa gactgggacc aggaaagcca ggtctaaaat tcaatggccc accaccgcca    1320
ccgccaccac caccaccca cttactatca tgctggctgc ctccatttcc ttctggacca    1380
ccaataattc ccccaccacc tcccatatgt ccagattctc ttgatgatgc tgatgctttg    1440
ggaagtatgt taatttcatg gtacatgagt ggctatcata ctggctatta tatgggtttt    1500
agacaaaatc aaaaagaagg aaggtgctca cattccttaa attaagaatt gcaccaccag    1560
gcctgatagg ccctgtgcct tctagttgcc agccatctgt tgtttgcccc tccccgtgc    1620 cttccttgac cctggaaggt gccactccca ctgtcctttc ctaataaaat gaggaaattg    1680
catcgcattg tctgagtagg tgtcattcta ttctggggggg tggggtgggg caggacagca    1740 aggggagga ttgggaagac aatagcaggc atgcactagt ccactccctc tctgcgcgct    1800
cgctcgctca ctgaggccgg gcgaccaaag gtcgcccgac gcccgggctt tgcccgggcg    1860
```

<210> SEQ ID NO 6
<211> LENGTH: 2338
<212> TYPE: DNA
<213> ORGANISM: Artificial Sequence
<220> FEATURE:
<223> OTHER INFORMATION: Synthetic construct

<400> SEQUENCE: 6

```
ggccactccc tctctgcgcg ctcgctcgct cactgaggcc gggcgaccaa aggtcgcccg      60
acgcccgggc tttgcccggg cggcctcagt gagcgagcga gcgcgcagag agggagtggc     120
caactccatc actaggggtt cctggagggg tggagtcgtg acagatcaat tcggtaccct     180
agttattaat agtaatcaat tacggggtca ttagttcata gcccatatat ggagttccgc     240
gttacataac ttacggtaaa tggcccgcct ggctgaccgc ccaacgaccc ccgcccattg     300
acgtcaataa tgacgtatgt tcccatagta acgccaatag ggactttcca ttgacgtcaa     360
tgggtggact atttacggta aactgcccac ttggcagtac atcaagtgta tcatatgcca     420
agtacgcccc ctattgacgt caatgacggt aaatggcccg cctggcatta tgcccagtac     480
atgaccttat gggactttcc tacttggcag tacatctacg tattagtcat cgctattacc     540
atggtcgagg tgagccccac gttctgcttc actctcccca tctcccccc ctccccaccc     600 ccaattttgt atttatttat ttttaatta ttttgtgcag cgatggggc ggggggggg     660 gggggcgcg cgccaggcgg ggcggggcgg ggcgagggc ggggcgggc gaggcggaga     720 ggtgcggcgg cagccaatca gagcggcgcg ctccgaaagt ttccttttat ggcgaggcgg     780
cggcggcggc ggccctataa aaagcgaagc gcgcggcggg cggagtcgc tgcgacgctg     840 ccttcgcccc gtgccccgct ccgccgccgc ctcgcgccgc ccgccccggc tctgactgac     900
cgcgttactc ccacaggtga gcgggcggga cggccttctc ctccgggctg taattagcgc     960
ttggtttaat gacggcttgt ttcttttctg tggctgcgtg aaagccttga ggggctccgg    1020
gagctagagc ctctgctaac catgttcatg ccttcttctt tttcctacag ctcctgggca    1080
acgtgctggt tattgtgctg tctcatcatt ttggcaaaga attttggaac tcgaattcat    1140
ggcgatgagc agcggcggca gtggtggcgg cgtcccggag caggaggatt ccgtgctgtt    1200
ccggcgcggc acaggccaga gcgatgattc tgacatttgg gatgatacag cactgataaa    1260
agcatatgat aaagctgtgg cttcatttaa gcatgctcta aagaatggtg acatttgtga    1320
aacttcgggt aaaccaaaaa ccacacctaa agaaaacct gctaagaaga ataaagccaa    1380
aaagaagaat actgcagctt ccttacaaca gtggaaagtt ggggacaaat gttctgccat    1440
ttggtcagaa gacggttgca tttacccagc taccattgct tcaattgatt ttaagagaga    1500
```

```
aacctgtgtt gtggtttaca ctggatatgg aaatagagag gagcaaaatc tgtccgatct    1560
actttcccca atctgtgaag tagctaataa tatagaacag aatgctcaag agaatgaaaa    1620
tgaaagccaa gtttcaacag atgaaagtga gaactccagg tctcctggaa ataaatcaga    1680
taacatcaag cccaaatctg ctccatgaaa ctcttttctc cctccaccac cccccatgcc    1740
agggccaaga ctgggaccag gaaagccagg tctaaaattc aatggcccac caccgccacc    1800
gccaccacca ccaccccact tactatcatg ctggctgcct ccatttcctt ctggaccacc    1860
aataattccc ccaccacctc ccatatgtcc agattctctt gatgatgctg atgctttggg    1920
aagtatgtta atttcatggt acatgagtgg ctatcatact ggctattata tgggtttcag    1980
acaaaatcaa aaagaaggaa ggtgctcaca ttccttaaat taagaattgc accaccaggc    2040
ctgataggcc ctgtgccttc tagttgccag ccatctgttg tttgcccctc ccccgtgcct    2100
tccttgaccc tggaaggtgc cactcccact gtcctttcct aataaaatga ggaaattgca    2160
tcgcattgtc tgagtaggtg tcattctatt ctgggggtg gggtggggca ggacagcaag    2220
ggggaggatt gggaagacaa tagcaggcat gcactagtcc actccctctc tgcgcgctcg    2280
ctcgctcact gaggccgggc gaccaaaggt cgcccgacgc ccgggctttg cccgggcg     2338
```

<210> SEQ ID NO 7
<211> LENGTH: 78
<212> TYPE: DNA
<213> ORGANISM: Artificial Sequence
<220> FEATURE:
<223> OTHER INFORMATION: Synthetic construct

<400> SEQUENCE: 7

```
cactccctct ctgcgcgctc gctcgctcac tgaggccggg cgaccaaagg tcgcccacgc      60
ccgggctttg cccgggcg                                                    78
```